(12) United States Patent
Geister

(10) Patent No.: US 12,402,893 B2
(45) Date of Patent: Sep. 2, 2025

(54) BONE PUNCHES

(71) Applicant: Geister Medizintechnik GmbH, Tuttlingen (DE)

(72) Inventor: Christian Geister, Tuttlingen (DE)

(73) Assignee: Geister Medizintechnik GmbH, Tuttlingen (DE)

( * ) Notice: Subject to any disclaimer, the term of this patent is extended or adjusted under 35 U.S.C. 154(b) by 18 days.

(21) Appl. No.: 18/225,518

(22) Filed: Jul. 24, 2023

(65) Prior Publication Data

US 2024/0023975 A1 Jan. 25, 2024

(30) Foreign Application Priority Data

Jul. 22, 2022 (EP) ..................................... 22186484

(51) Int. Cl.
*A61B 17/16* (2006.01)

(52) U.S. Cl.
CPC ................ *A61B 17/1611* (2013.01)

(58) Field of Classification Search
CPC .... A61B 2017/1602; A61B 2017/1604; A61B 17/1606; A61B 17/1611
See application file for complete search history.

(56) References Cited

U.S. PATENT DOCUMENTS

| | | | | |
|---|---|---|---|---|
| 6,126,674 A | * | 10/2000 | Janzen | A61B 17/1611 606/1 |
| 7,377,933 B2 | * | 5/2008 | Martin | A61B 17/1611 606/208 |
| 8,206,408 B2 | | 6/2012 | Rebstock | |
| 8,801,714 B1 | * | 8/2014 | Bodor | A61B 17/1611 600/564 |
| 9,572,554 B2 | * | 2/2017 | Dmuschewsky | A61B 17/1608 |
| 9,867,626 B2 | * | 1/2018 | Fetzer | A61B 17/1604 |

FOREIGN PATENT DOCUMENTS

| | | |
|---|---|---|
| DE | 10022908 | 11/2001 |
| DE | 102010006846 | 9/2010 |

(Continued)

OTHER PUBLICATIONS

Decision to Grant a European patent pursuant to Article 97(1) EPC in European Application No. 22186484.6, including English language translation.

(Continued)

*Primary Examiner* — Kevin T Truong
*Assistant Examiner* — Diana Jones
(74) *Attorney, Agent, or Firm* — FisherBroyles LLP

(57) ABSTRACT

Disclosed is a disassemblable bone punch comprising a shaft and a handle, wherein the shaft comprises a first shaft part and a second shaft part, wherein the first shaft part comprises at least one first guiding element, and the second shaft part comprises at least one second guiding element, wherein the first shaft part is connected to the second shaft part such that the first guiding element is in engagement with the second guiding element and the first shaft part is movable parallel to a proximal-to-distal direction relative to the second shaft part, wherein the shaft is movable into a disassembly position, into a neutral position and into a punching position.

13 Claims, 18 Drawing Sheets

(56) References Cited

FOREIGN PATENT DOCUMENTS

| DE | 102011109721 | 2/2013 |
|----|--------------|--------|
| DE | 102013112429 | 5/2015 |

OTHER PUBLICATIONS

European Search Report mailed Nov. 26, 2022, in European Application No. 22 18 6484.6.
Decision to Grant a European patent pursuant to Article 97(1) EPC in European Application No. 22186484.6, mailed Jun. 27, 2024, including English language translation.
Communication under Rule 71(3) EPC in European Application No. 22186484.6, mailed Feb. 16, 2024, including English language translation.
Communication pursuant to Article 94 (3) EPC in European Application No. 22186484.6, mailed Mar. 7, 2023, including English language translation.

* cited by examiner

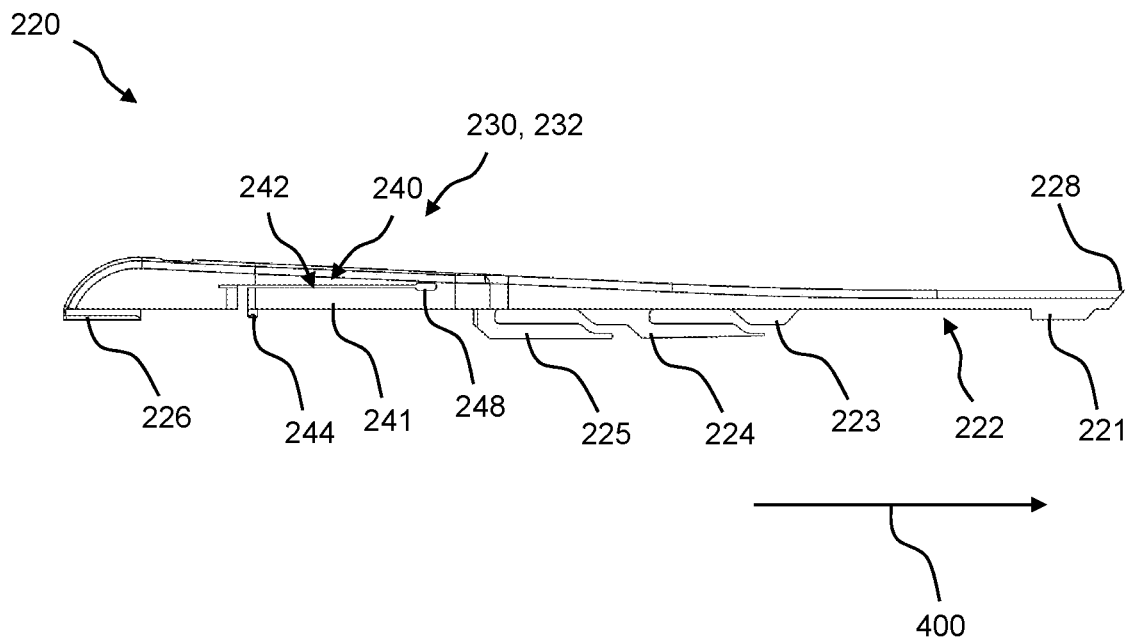
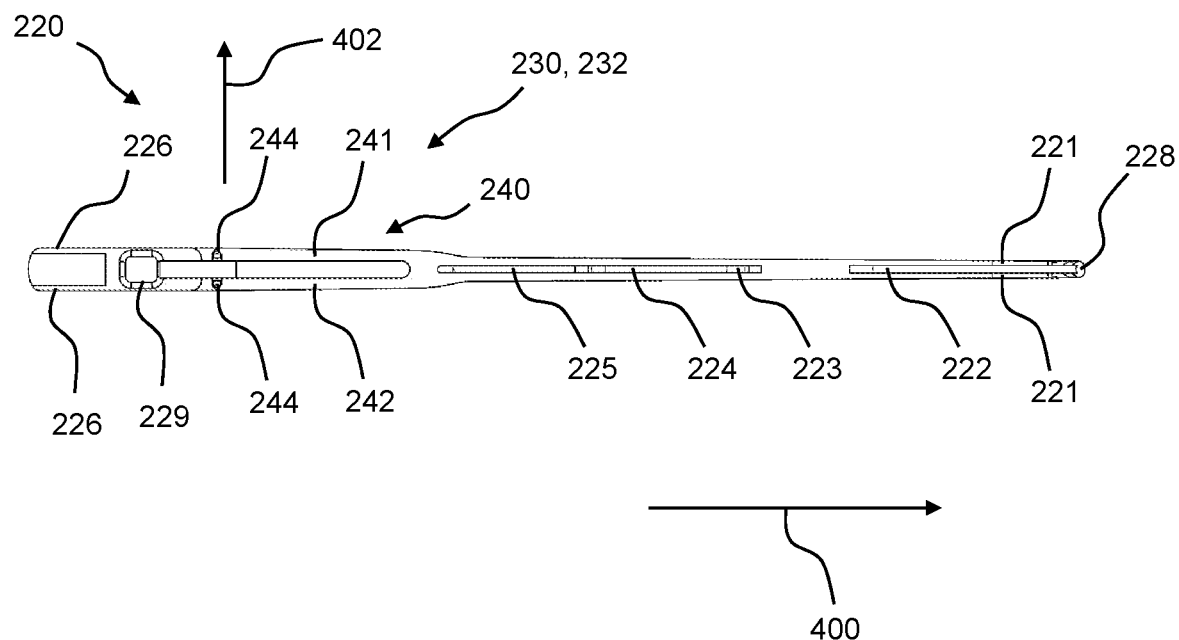

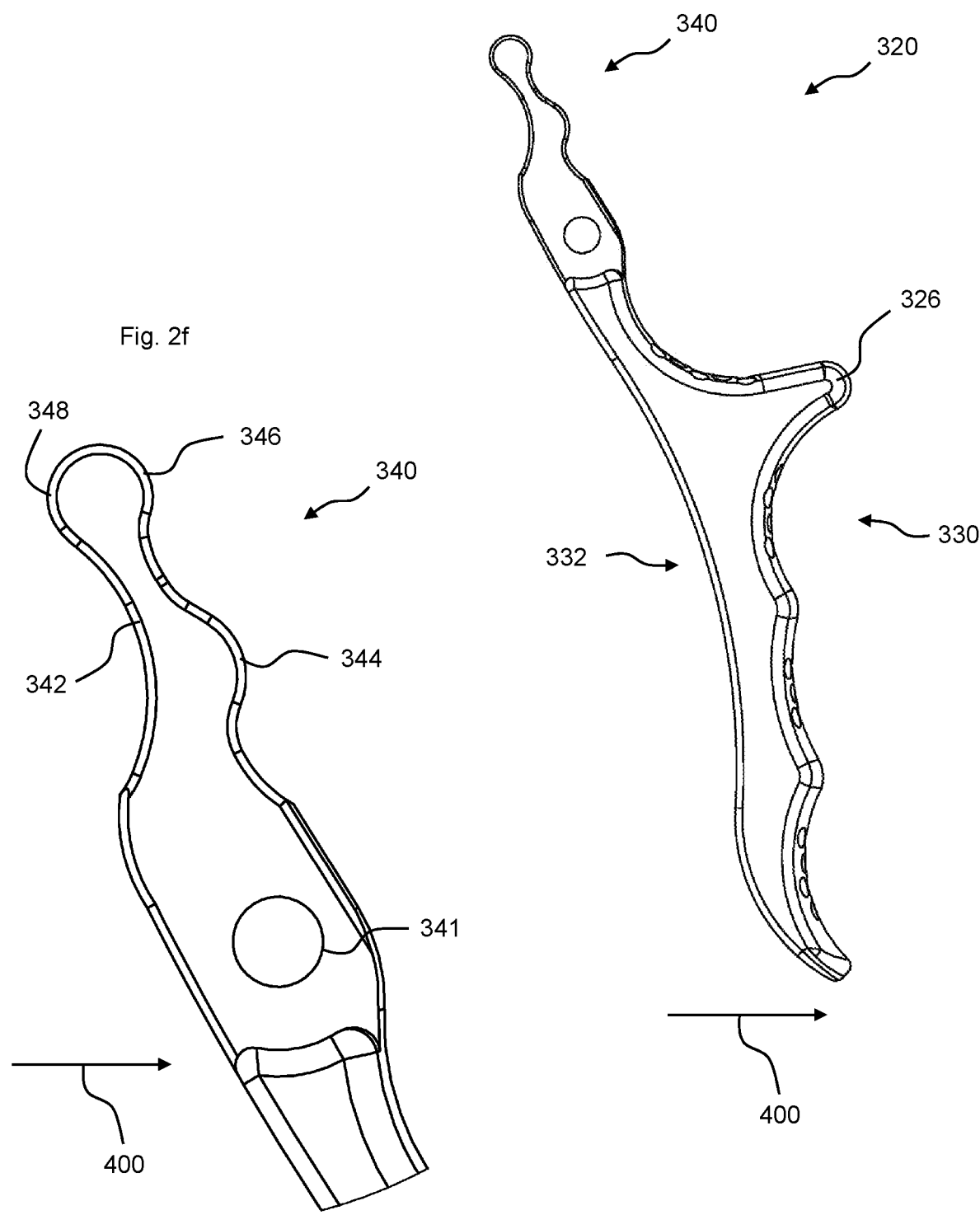

BONE PUNCHES

FIELD OF THE INVENTION

The invention relates to a disassemblable bone punches.

STATE OF THE ART

Bone punches are known from the state of the art and are used for the surgical removal of bone, ligaments, cartilage and related tissue in various medical disciplines. As high-priced special products, they are designed for multiple use and must be cleaned after each operation. To support the cleaning process, the bone punches can also be designed to be disassembled. Disassemblable bone punches are also known from the prior art, but compared to non-disassemblable bone punches, they have a large number of additional components which are intended on the one hand to ensure disassembly security, i.e. safe handling during surgical use, and on the other hand to enable them to be disassembled. The disassembly itself, and in particular the release of the disassembly security, then takes place in several steps. In most cases, it is already necessary to remove components for this step. A certain sequence of steps must also be followed when releasing the disassembly security, otherwise the bone punches cannot be disassembled or may even be damaged. In addition, the components used for securing take up extra space, cause additional weight and therefore hinder or complicate the regular, i.e. operational, use of the bone punches.

REPRESENTATION OF THE INVENTION

It is thus the object of the present invention to provide a disassemblable bone punches which has good and safe handling properties and is robust and easy to disassemble.

The object is solved by a disassemblable bone punches according to claim 1. Further features developing the invention are subject of the dependent claims.

A disassemblable bone punch according to the invention comprises a shaft and a handle, wherein the shaft comprises a first shaft part and a second shaft part, wherein the first shaft part comprises at least one first guiding element, and the second shaft part comprises at least one second guiding element, wherein the first shaft part is connected to the second shaft part such that the first guiding element is in engagement with the second guiding element and the first shaft part is movable parallel to a proximal-to-distal direction relative to the second shaft part, wherein the shaft is movable into a disassembly position, into a neutral position and into a punching position, wherein the handle comprises a first handle portion and a second handle portion, wherein the first handle portion is movably connected to the second shaft part, wherein the second handle portion is connected to the second shaft part, wherein by a first movement of the first handle portion the shaft is displaceable from the neutral position into the punching position, characterized in that by a second movement of the first handle portion the shaft can be moved from the neutral position into the disassembly position.

Thus, a disassemblable bone punches is provided, which has a good and safe handling and is robust and easy to disassemble and has the lowest possible number of components.

The neutral position is the position in which the bone punches is in the operating state without any external force being applied.

The punching position is the position to which the bone punches is moved during its main use in order to punch the tissue to be removed. For this purpose, the shaft may have a punching element and a punch intake, whereby during punching, i.e. when the shaft is moved into the punching position, the punching element moves into the punch intake while the tissue to be removed is located between the two elements. The tissue to be removed is then removed or separated by further retraction of the punching element into the punch intake.

The disassembly position is the position in which the shaft and preferably the entire bone punches can be separated into its individual parts. In this position, the first shaft part can be separated from the second shaft part and the first handle portion can be separated from the second handle portion.

The proximal-distal direction is the direction from the proximal end, i.e. the end closest to the user, to the distal end, i.e. the end furthest away from the user, during regular use of the bone punches.

The bone punches is preferably configured in such a way that the first movement moves the first handle portion towards the second handle portion. Preferably, the bone punches is also configured in such a way that the second movement can be performed away from, in particular opposite to, the first movement.

Preferably, the first handle portion is connected to the second shaft part via a connecting device and the corresponding movability is enabled by the connecting device.

Preferably, the first handle portion is connected to the second shaft part in such a way that the first handle portion can be rotated about a point located in the vicinity or in the area of the second shaft part.

Preferably, the first handle portion is further arranged in such a way that the first handle portion, preferably its head region, touches the first shaft part.

Preferably, the connection between the second handle portion and the second shaft part is fixed in the entire operating state and is also not intended to be detachable for disinfection, i.e. the second handle portion is not movable relative to the second shaft part. The connection can be a non-detachable joint, but also a detachable connection, such as a plug-in or screw connection.

Preferably, the first shaft part comprises a locking area, wherein the locking area is movable from a neutral status to an unlocking status, wherein the locking area is configured such that, when the locking area is in the neutral status, moving of the shaft into the disassembly position is prevented and, by the second movement, the locking area is simultaneously moved into the unlocking status and the shaft is moved into the disassembly position. Thus, it can be prevented that the shaft is unintentionally moved into the disassembly position, which may increase the safety of the bone punches. The locking area can be configured as a locking mechanism.

Preferably, the locking area comprises a deflectable spring area, wherein the locking area is movable into the unlocking status by deflecting the spring area. This simplifies the disassembly of the bone punches.

Preferably, the spring area is configured to be deflectable substantially perpendicular to the proximal distal direction. Thus, it can be prevented that during regular use, while the shaft part is moved parallel to or along the proximal-distal direction, the locking area is unintentionally moved into the unlocking status, which may increase the safety of the bone punches.

Preferably, the spring area is deflectable substantially parallel to a horizontal direction. Thus, a low height of the bone punches can be achieved in a vertical direction, which increases their handling properties. The horizontal direction is located in a horizontal plane and is aligned perpendicular to the proximal-distal direction. The horizontal plane results with respect to the orientation of the bone punches during regular operation or during their main use. The horizontal plane is oriented substantially parallel to the shaft and perpendicular to the handle.

The vertical direction is oriented perpendicular to the proximal-distal direction and perpendicular to the horizontal direction.

Preferably, the spring area is deflectable substantially parallel to a vertical direction. Thus, a small width of the bone punches can be achieved in a horizontal direction, which may increase the handling properties of the same.

Preferably, the spring area comprises a loose end and a fixed end, with the loose end comprising the greatest deflectability and the fixed end being non-deflectable.

Preferably, the spring area comprises a recess, which is in particular rounded or curved and is preferably arranged at the fixed end of the spring area. This prevents stress cracks from forming in the spring area when it is deflected, particularly in the case of regular repeated deflections, which may increase the lifetime of the bone punches. Here, the recess acts as a kind of undercut.

Preferably, the second shaft part comprises a fixing area, the fixing area being configured and arranged to interact with the locking area such that if the locking area is in the neutral status, additional resistance is provided by the fixing area opposing the movement of the shaft into the disassembly position. Thus, it can be additionally prevented that the locking area is unintentionally moved into the unlocking position, whereby the safety of the bone punches can be additionally increased. In this context, interacting is understood to be preferably the corresponding interaction of the fixing area with the locking area.

Preferably, the locking area comprises at least one first resistance element and/or the fixing area comprises at least one second resistance element, wherein the first resistance element and/or the second resistance element is/are arranged and configured such that an additional resistance opposes the movement of the locking area into the unlocking status. Thus, the safety of the bone punches can be additionally increased.

Preferably, the disassemblable bone punches comprises a first resistance element and a second resistance element, wherein the first resistance element and the second resistance element are interactively arranged and configured such that additional resistance opposes the movement of the locking area into the unlocking status. Thus, the safety of the bone punches can be additionally increased.

Preferably, the first resistance element is configured as a projection and/or the second resistance element is configured as a bulge. Thus, the manufacturing of bone punches can be simplified and their robustness can be increased.

According to a preferred alternative, the first resistance element is configured as a bulge and/or the second resistance element is configured as a cylinder. Thus, the manufacturing of the bone punches can be simplified and their robustness can be increased.

Preferably, the bone punches further comprises a first stop element preferably arranged in the second shaft part, wherein the first stop element is configured and further arranged such that the movability of the first handle portion is limited proximally. Thus, it can be prevented that the locking area is deflected further or loaded more than necessary or intended, which may increase the lifetime and safety of the bone punches.

Preferably, the bone punches further comprises a second stop element preferably arranged in the second shaft portion, wherein the second stop element is configured and further arranged such that the movability of the first handle portion is limited distally. Thus, it can be prevented that the shaft or the first shaft part is deflected further than the punching position indicates or results from this punching position, whereby the lifetime and the safety of the bone punches can be increased.

Preferably, the bone punches further comprise a return member preferably arranged in the second shaft part, wherein the return member is configured and further arranged such that after performing the first movement, the shaft is automatically displaced from the punching position back to the neutral position and, preferably the first movement is opposed by a resistance, preferably an increasing resistance. Thus, during the main use of the bone punches, no force has to be applied by the operator to reset or move the shaft from the punching position to the neutral position, which can increase the handling properties. Furthermore, this can easily provide feedback to the operator regarding the current position or positioning of the shaft during the main use of the bone punches. The increasing resistance may be achieved by the return member having a compression spring. The resistance is increasing in that it increases as the first movement progresses, in particular linearly. In particular, the resistance starts to increase immediately after or in the neutral position. I.e. in the neutral position the resistance is lowest and immediately before the end of the first movement or at the end of the first movement, i.e. in the punching position, the resistance is highest.

BRIEF DESCRIPTION OF THE DRAWINGS

FIG. 2a shows a side view of a first shaft part of the bone punches displayed in FIGS. 1a to 1e.

FIG. 2b shows a bottom view of the first shaft part displayed in FIG. 2a.

FIG. 2e shows a first handle portion of the bone punches displayed in FIGS. 1a to 1e.

FIG. 2f shows a handle head of the first handle portion displayed in FIG. 2e in a side view.

DESCRIPTION OF THE PREFERRED EMBODIMENTS

Figure 1A:
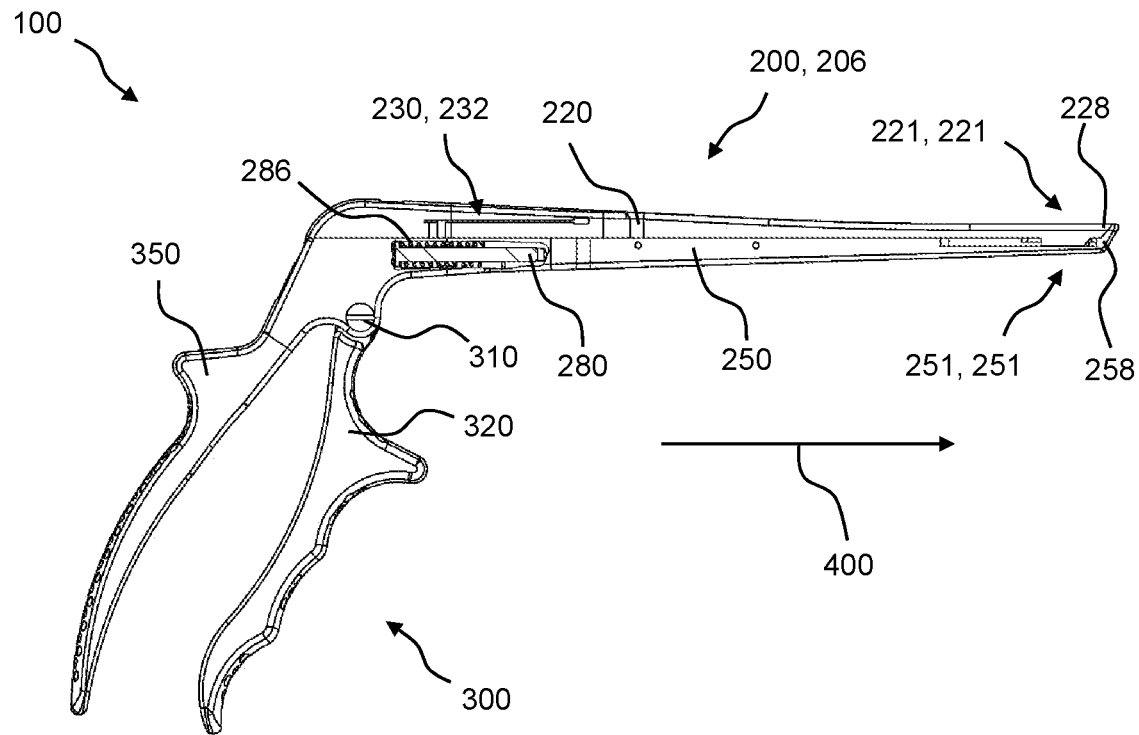
FIG. 1a shows a bone punches with a proximally arranged locking area in a punching position.

FIG. 1a shows a bone punches 100 with a proximally arranged locking area 230 in a punching position 206. The bone punches 100 comprises a handle 300. The handle 300 comprises a first handle portion 320 and a second handle portion 350. The bone punches 100 further comprises a shaft 200, which is shown to be in the punching position 206. The shaft 200 comprises a first shaft portion 220 and a second shaft portion 250. The locking area 230 is part of the second shaft part 250 and is in a neutral status 232. The second shaft part 250 is located below the first shaft part 220 as illustrated. The second handle portion 350 is connected to the second shaft part 250. The first handle portion 320 is movably, in this case rotatably, connected to the second shaft part 250 via a connecting device 310. The bone punches 100 further comprises a return member 280 disposed in the second shaft part 250 and oriented along a proximal-distal direction 400. The return member 280 further comprises a spring 286. In the area of the return member 280, a partial section is shown in FIG. 1a. The longitudinal direction of the shaft 200 is parallel to the proximal-distal direction 400. The first shaft part 220 comprises a punching element 228 disposed at the distal end of the first shaft part 220. The second shaft part 250 comprises a punch intake 258 disposed at the distal end of the second shaft part 250. In the shown punching position 206, the punching element 228 is positioned in or in contact with the punch intake 258. The first shaft part 220 comprises two first guiding elements 221 arranged in the distal region immediately in front of the punching element 228. The second shaft part 250 comprises two second guiding elements 251, which are arranged in the distal area directly in front of the punch intake 258.

Figure 1B:
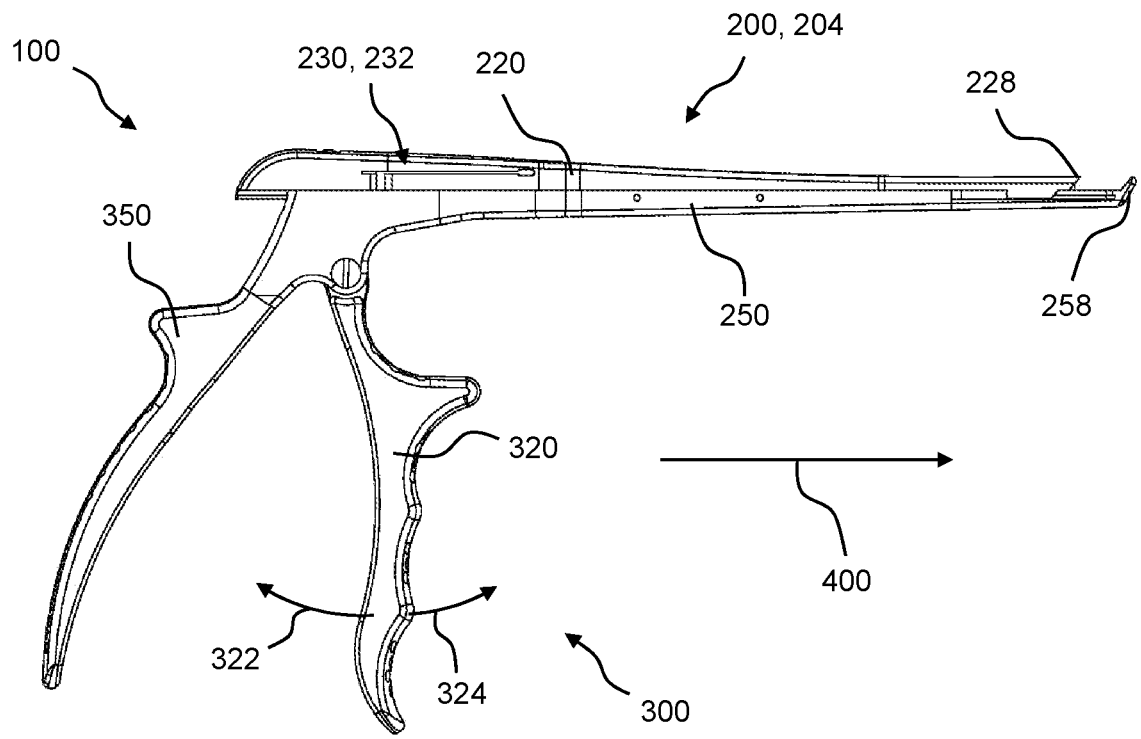
FIG. 1b shows the bone punches displayed in FIG. 1a in a neutral position.

FIG. 1b shows the bone punches 100 displayed in FIG. 1a in a neutral position 204. In the neutral position 204, the first shaft part 220 is positioned further distally than in the punching position 206 (cf. FIG. 1a). Accordingly, the punching element 228 is also spaced from the punch intake 258 so that tissue to be punched can be received in the distal shaft area. As in the punching position 206, the locking area 230 is in the neutral status 232. If the first handle portion 320 is deflected substantially proximally, i.e. along a first movement 322, the shaft 200 is deflected into or towards the punching position 206. The movement 322 follows a circular path, since the first handle portion 320—as described above in connection with FIG. 1a—is rotatably connected to the second shaft part 250 by means of the connecting device 310. The rotation takes place around an axis that is located in the area of the connecting device 310. If the first handle portion 320 is deflected distally, i.e. a second movement 324 is executed, the shaft 200 is moved into a disassembly position 202 (cf. FIG. 1c). The second movement 324 is executed in the opposite direction to the first movement 322 and also follows a circular path or around the above-mentioned axis in the region of the connecting device 310.

Figure 1C:
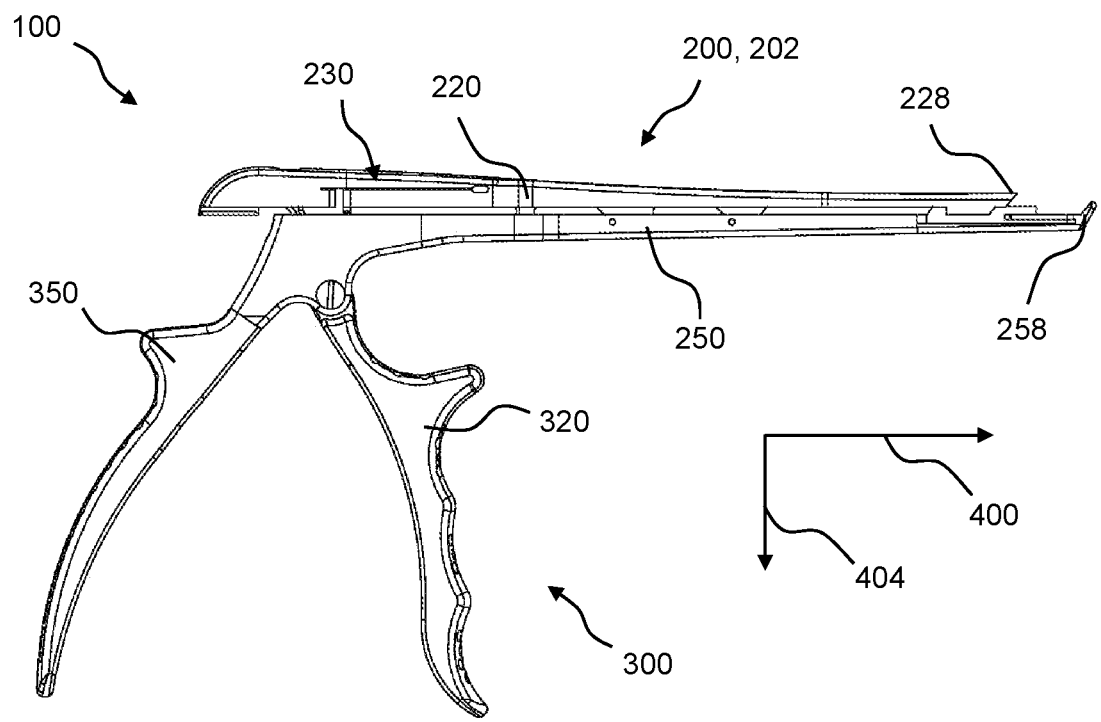
FIG. 1c shows the bone punches displayed in FIGS. 1a and 1b in a disassembly position.

FIG. 1c shows the bone punches 100 displayed in FIGS. 1a and 1b in the disassembly position 202. Along the proximal-distal direction 400, the first handle portion 320 is maximally spaced from the second handle portion 350. In the disassembly position 202, the first shaft portion 220 is positioned away from the second shaft portion 250 along a vertical direction 404 that is perpendicular to the proximal-distal direction 400 and substantially along the longitudinal axis of the handle 300. At the time of displacement of the shaft 200 from the neutral position 204 to the disassembly position 202, the locking area 230 is deflected into an unlocking status 234 (cf. FIG. 6c).

Figure 1D:
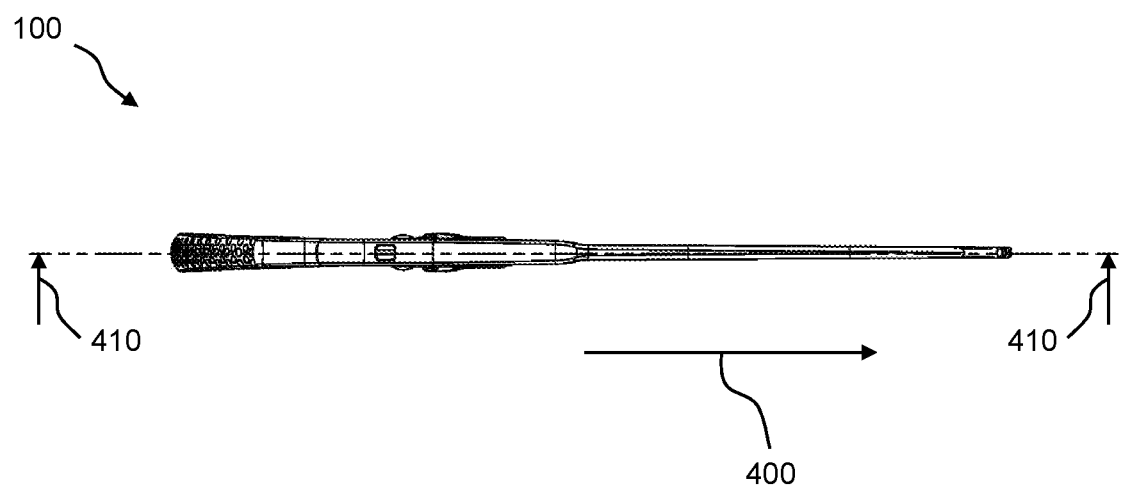
FIG. 1d shows the bone punches displayed in FIGS. 1a to 1c in a top view.

FIG. 1d shows the bone punches 100 displayed in FIGS. 1a to 1c in a top view. An intersection line is drawn centrally along the proximal-distal direction 400.

Figure 1E:
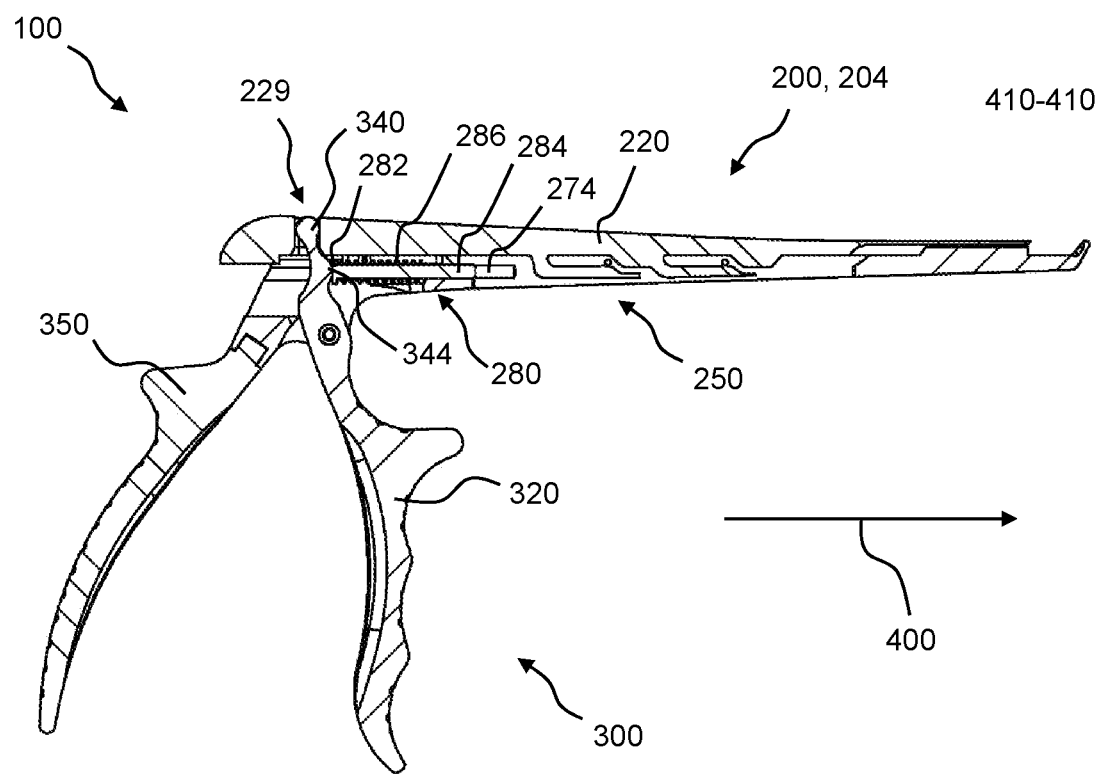
FIG. 1e shows the bone punches displayed in FIGS. 1a to 1d in the neutral position displayed in FIG. 1b in a sectional view.

FIG. 1e shows the bone punches 100 displayed in FIGS. 1a to 1d in the neutral position 204 displayed in FIG. 1b in a sectional view 410-410 along the sectional line displayed in FIG. 1d. The return member 280 (cf. FIG. 5e) comprises a shaft 284 oriented along the proximal-distal direction 400. The second shaft part 250 further comprises a guiding opening 274 in which the return member 280 is received or in which the shaft 284 is guided. The return member 280 further comprises a stop 282 which is oriented proximally. The return member 280 further comprises a spring 286 that is mounted on the shaft 284. The first handle portion 320 comprises a handle head 340 in the upper region. The first shaft portion 220 comprises a guiding opening 229 in the proximal region (cf. FIGS. 2b, 4b). The first handle portion 320 further comprises a first load transfer area 344 arranged at the handle head 340. The first load transfer area 344 is distally oriented and arranged in contact with the stop 282 such that by the first movement 322 (cf. FIG. 1b), the return member 280 is moved distally into the guiding opening 274. Furthermore, by the first movement 322 the upper end of the handle head 340 is moved distally, whereby the first shaft part 220 is also moved distally via the guiding opening 229 and finally the shaft 200 is moved into the punching position 202 (cf. FIG. 1*a*).

FIG. 2*a* shows the first shaft part 220 of the bone punches 100 displayed in FIGS. 1*a* to 1*e* in a side view. Opposite to the proximal-distal direction 400, i.e. from distal to proximal, the first shaft part 220 further comprises, in addition to the two first guiding elements 221 in sequence, another four first guiding elements 222, 223, 224, 225 and another two guiding elements 226. The locking area 230 is located in the neutral status 232 and comprises a spring area 240 which comprises a fixed, i.e. non-deflectable, end towards the distal end and a loose, i.e. maximally deflectable, end towards the proximal end. The spring area 240 comprises a first spring arm 241 and a second spring arm 242, which are arranged opposite each other (cf. FIG. 2*b*). The second spring arm 242 is shown covered by the first spring arm 241 in FIG. 2*a*. The spring area 240 comprises a recess 248 arranged at the fixed end of the spring area 240. The spring area 240 is rounded or curved. The first spring arm 241 and the second spring arm 242 each comprise a projection 244, wherein the projection 244 of the second spring arm 242 is covered herein by the projection 244 of the first spring arm 241.

FIG. 2*b* shows a bottom view of the first shaft part 220 displayed in FIG. 2*a*. The guiding opening 229 is continuous from bottom to top. The first spring arm 241 and the second spring arm 242 are each formed such that their loose ends, i.e., their proximal ends are deflectable along a horizontal direction 402. The locking area 230 is located in the neutral status 232.

Figure 2C:
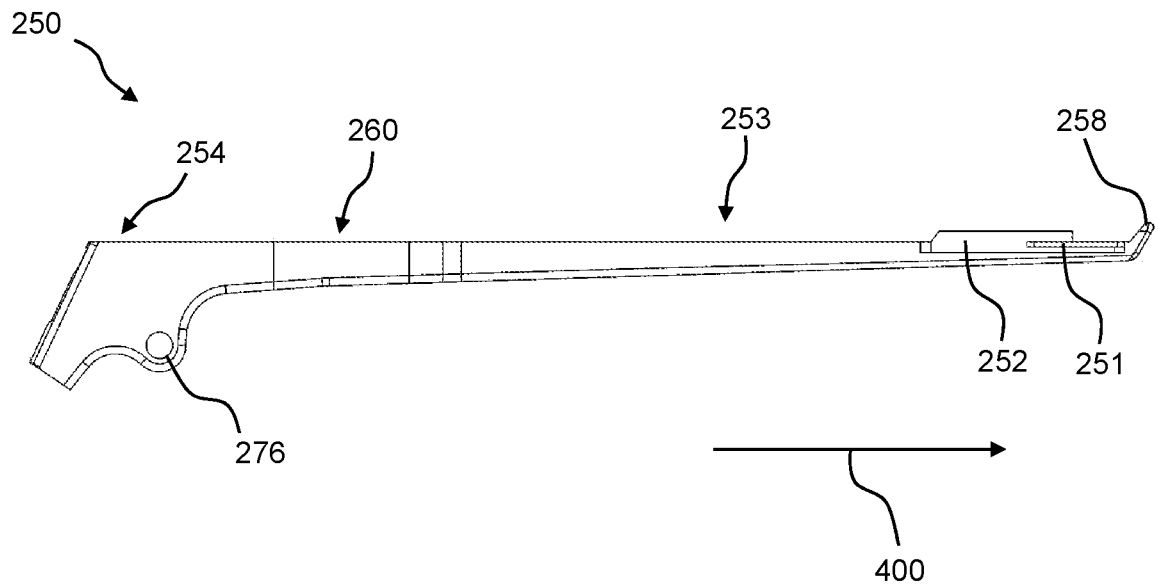
FIG. 2c shows a side view of a second shaft part of the bone punches displayed in FIGS. 1a to 1e.

FIG. 2*c* shows the second shaft part 250 of the bone punches 100 displayed in FIGS. 1*a* to 1*e* in a side view. Opposite the proximal-distal direction 400, i.e. from distal to proximal, the second shaft part 250 comprises, in addition to the two second guiding elements 251 following one another, a further second guiding element 252, a further second guiding element 253 and two further guiding elements 254. The first guiding elements 221, 222, 223, 224, 225, 226 and the second guiding elements 251, 252, 253, 254 are configured to complement each other in such a way that the first shaft part 220 can be moved along the second shaft part 250 in the proximal-distal direction 400, i.e. can be moved from the neutral position 204 to the punching position 206 and vice versa. The two first guiding elements 221 and the two second guiding elements 251 are engaged with each other in the punching position 202 and in the neutral position 204, as are the first guiding element 222 and the second guiding element 252, the first guiding elements 223, 224, 225 and the second guiding element 253, and the two first guiding elements 226 and the two second guiding elements 254. The second shaft part 250 further comprises a fixing area 260 that is complementary to the spring area 240 (cf. FIGS. 2*a*, 2*b*). The second shaft part 250 further comprises an intake 276, which is configured complementary to the intake of the connecting device 310 (cf. FIG. 1*a*).

Figure 2D:
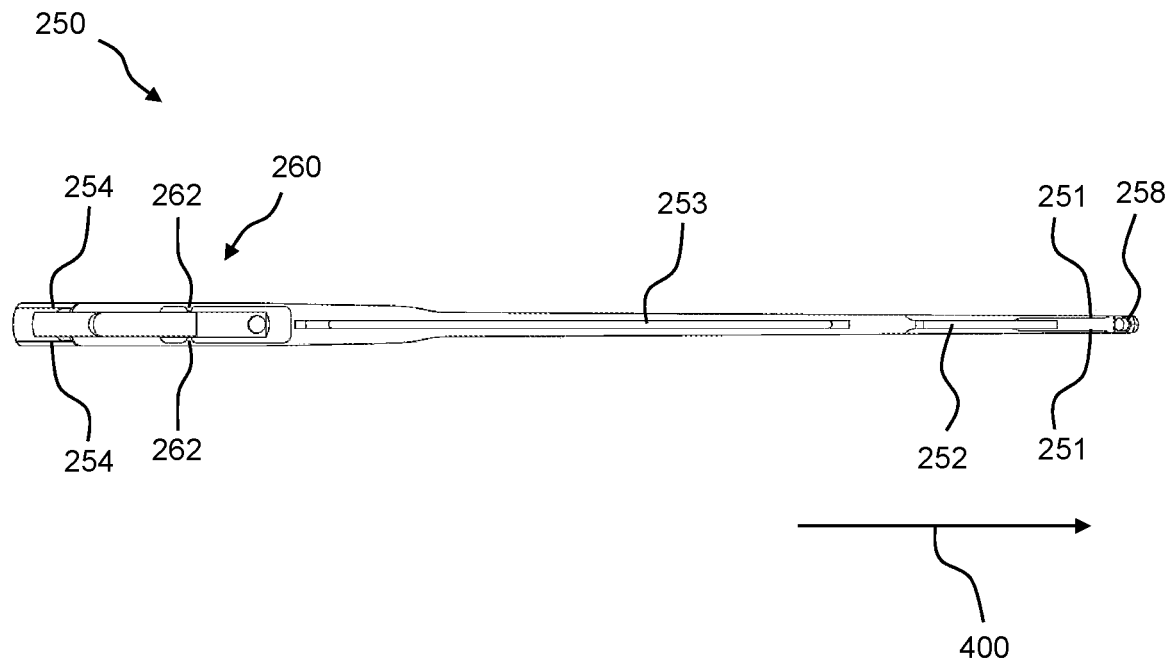
FIG. 2d shows a top view of the second shaft part displayed in FIG. 2c.

FIG. 2*d* shows a top view of the second shaft part 250 displayed in FIG. 2*c*. The fixing area 260 comprises two opposite bulges 262.

FIG. 2*e* shows the first handle portion 320 of the bone punches 100 displayed in FIGS. 1*a* to 1*e* according to the orientation present at the disassembly position 202. The first handle portion 320 comprises a first handle side 330 oriented distally and a second handle side 332 oriented proximally. On the first handle side 330, the first handle portion 320 comprises a protrusion 326 that provides a more secure and ergonomic grip for the user during primary use of the bone punches 100. Positioning of the user's index finger is intended above the protrusion 326, and positioning of the user's middle, ring, and pinky fingers is intended below the protrusion.

FIG. 2*f* shows the handle head 340 of the first handle portion 320 displayed in FIG. 2*e* in a side view. The handle head 340 comprises an intake 341, which is configured for intake of the connecting device 310 (cf. FIG. 1*a*) and is aligned with the intake 276 of the second shaft part 250 (cf. FIG. 2*c*). In the upper region, the handle head 340 further comprises a second load transfer area 346 and a third load transfer area 348. The second load transfer area 346 is oriented distally and is configured such that during the first movement 322 (cf. FIG. 1*b*) load can be transferred to the distal wall of the guiding opening 229 (cf. FIG. 2*b*), which causes the first shaft part 220 to move distally. The third load transfer area 348 is oriented proximally and is configured to transfer load to the proximal wall of the guiding opening 229 (cf. FIG. 2*b*), causing the first shaft part 220 to move proximally and to move from the neutral position 204 to the disassembly position 202. The head area 340 further comprises a recess 342 that reduces moving masses, which can improve the handling properties of the bone punches 100. The first load transfer area 344, the second load transfer area 346 and the third load transfer area 348 are each bent or curved. This ensures that no tilting occurs when transferring the load from the first handle portion 320 along a circular path (cf. FIG. 1*b*) to the first shaft part 220 and to the return member 280, where an essentially linear movement is generated, and that the handle head 340 rolls on the first shaft part 220 and on the return member 280. This may increase the robustness of the bone punches 100 and improve its handling properties.

Figure 2G:
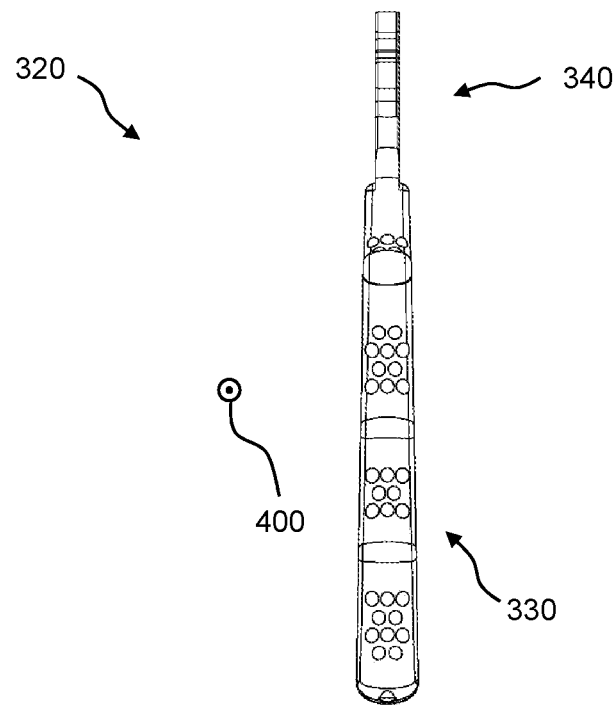
FIG. 2g shows a front view of the first handle portion displayed in FIG. 2e.

FIG. 2*g* shows the first handle portion 320 displayed in FIG. 2*e* in a front view, i.e. against the proximal-distal direction 400. The first handle side 330 is broader than the handle head 340. The handle head 340 is narrow enough to be accommodated in the second shaft part 250 (cf. FIGS. 2*c*, 2*d*).

Figure 2H:
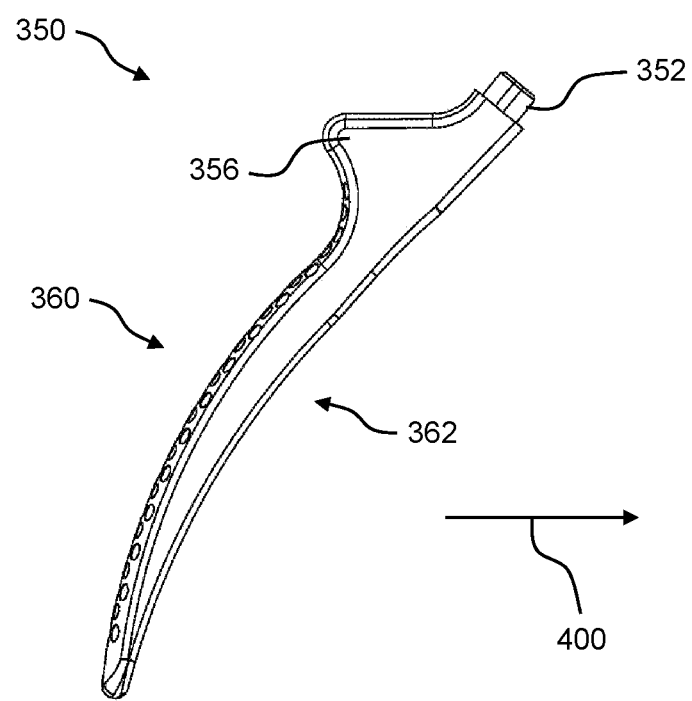
FIG. 2h shows a side view of a second handle portion of the bone punches displayed in FIGS. 1a to 1e.

FIG. 2*h* shows the second handle portion 350 of the bone punches 100 displayed in FIGS. 1*a* to 1*e* in a side view. The second handle portion 350 comprises a first handle side 360 oriented proximally and a second handle side 362 oriented distally. On the first handle side 360, the second handle portion 350 comprises a protrusion 356 that provides a more secure and ergonomic grip for the user during the main use of the bone punches 100. The protrusion 356 is configured to prevent the user's hand from sliding upward toward the proximal end of the shaft 200. For this purpose, the user's metacarpal region is intended to rest between the thumb and index finger immediately below the protrusion 356. The second handle portion 350 further comprises a plug element 352, which is arranged in the upper region of the second handle portion 350 and by means of which the second handle portion 350 is connected or joined to the second shaft part 250 (cf. FIG. 1*a*).

Figure 2I:
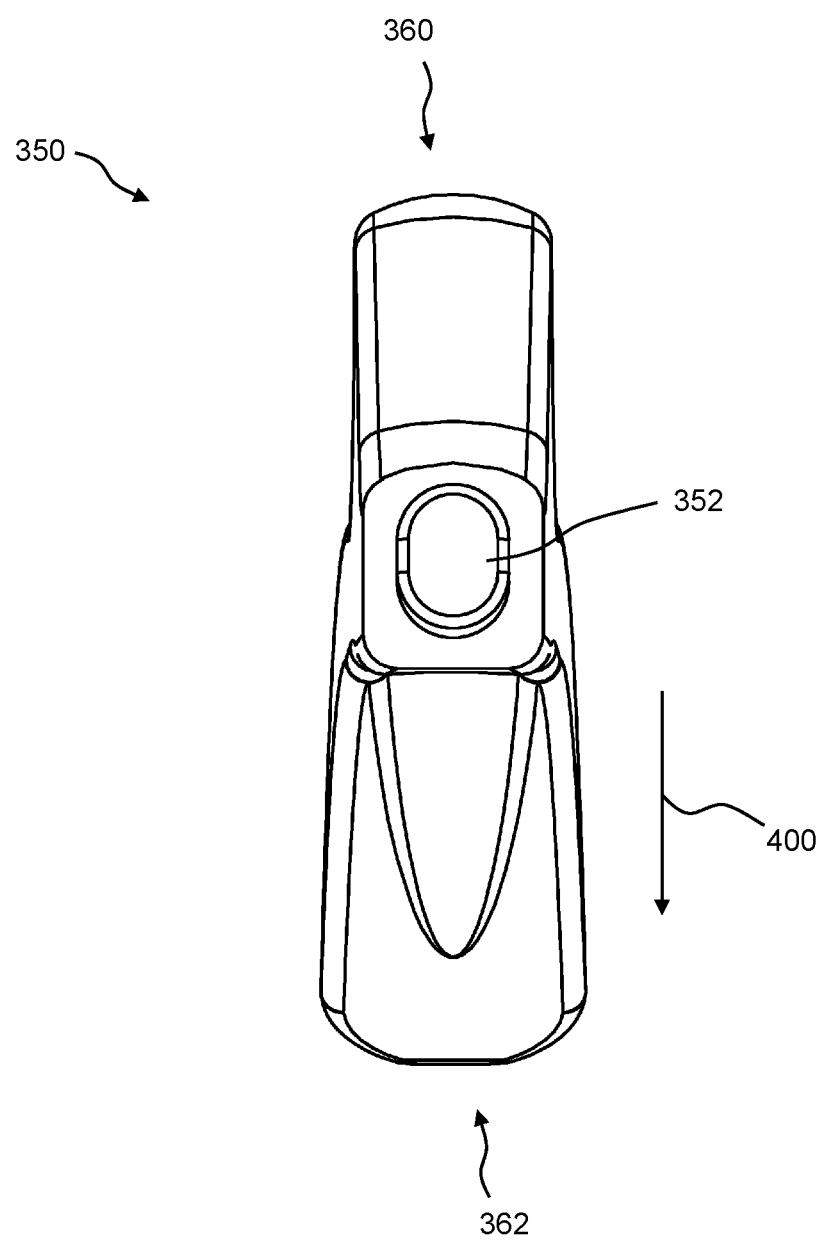
FIG. 2i shows the second handle portion displayed in FIG. 2h in an oblique top view.

FIG. 2*i* shows the second handle portion 350 displayed in FIG. 2*h* in an oblique view from above. The first handle side 360 is oriented upward in the illustration and the second handle side 362 is oriented downward. The plug element 352 comprises an oval cross-section. Thus, a good assemblability of the second handle portion 350 and the second shaft part 250 can be achieved. It is also possible that the plug element 352 comprises other cross-sections that, for example, support or improve the load transfer between the second shaft part 250 and the second handle portion or reduce deformation between these two components. Such cross sections may be, e.g., round, polygonal, but also cross- or star-shaped cross sections.

Figure 3A:
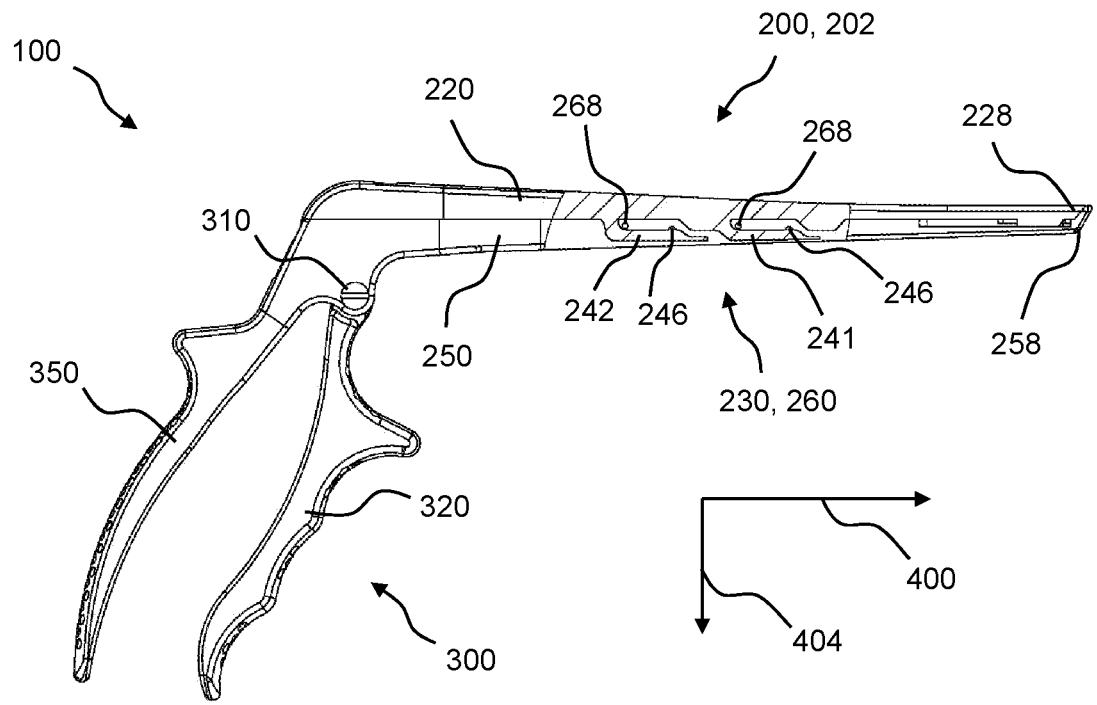
FIG. 3a shows another bone punches with a distally arranged locking area in a punching position.

FIG. 3a shows another bone punches 100 with a distally arranged locking area 230 in a punching position 202. In the area of the locking area 230, the bone punches 100 is shown in partial section. The first spring arm 241 and the second spring arm 242 are arranged one behind the other along the proximal-distal direction 400, with the first spring arm 241 being arranged more distally than the second spring arm 242. The locking area 230 and the fixing area 260 are arranged to engage with each other. The fixing area 260 comprises two cylinders 268. The first spring arm 241 and the second spring arm 242 each comprise a bulge 246. The two cylinders 268 are located at the proximal end of each of the first and second spring arms 241, 242 and at their fixed ends, respectively.

Figure 3B:
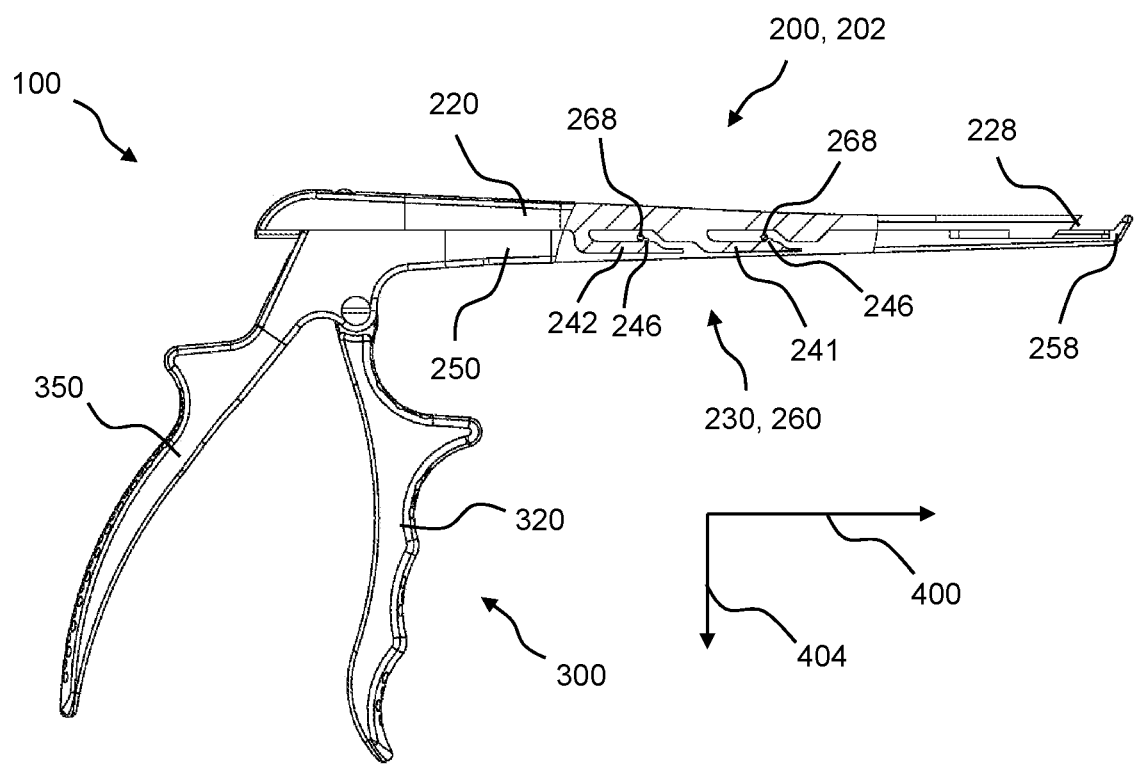
FIG. 3b shows the bone punches displayed in FIG. 3a in a neutral position.

FIG. 3b shows the bone punches 100 displayed in FIG. 3a in a neutral position 204. In the area of the locking area 230, the bone punches 100 is shown in partial section. The two cylinders 268 are each located immediately in front of the two bulges 246, i.e. further proximally than the two bulges 246. Accordingly, before the first shaft part 220 is displaced further proximally, the two cylinders 268 would have to overcome the two bulges 246. This would require the first and second spring arms 241, 242 to be deflected along the vertical direction 404, again creating space for the two cylinders 268 to slide past the two bulges 246. This situation is shown in FIG. 3c.

Figure 3C:
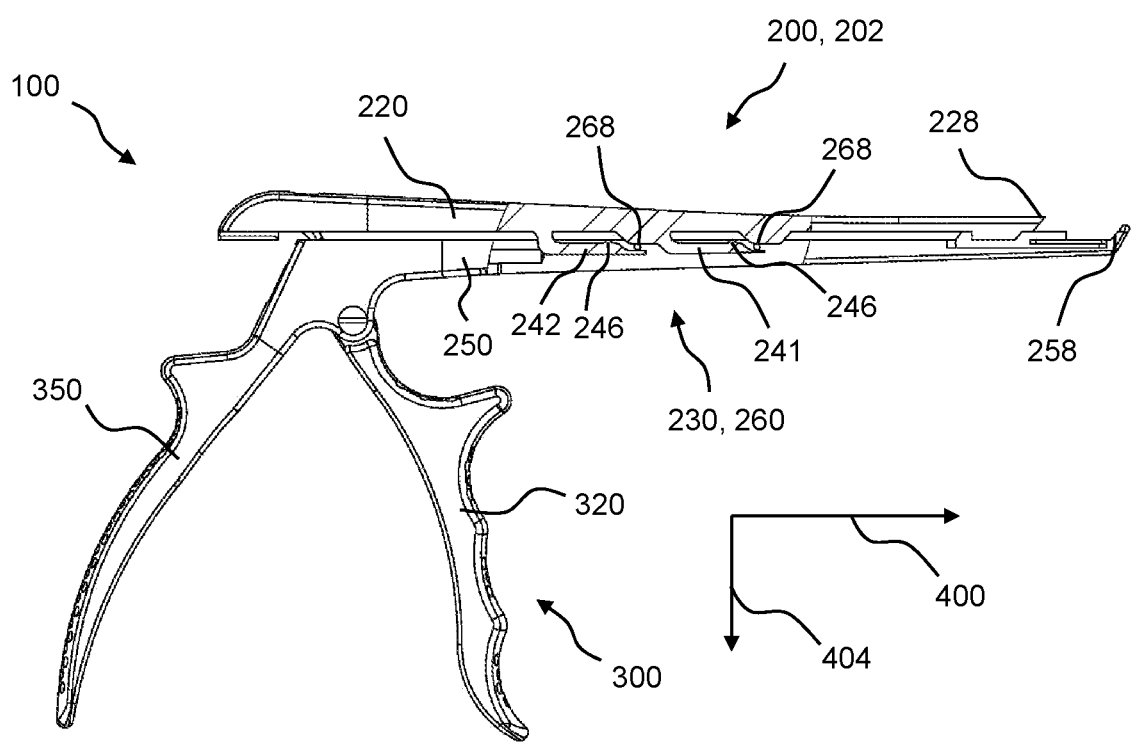
FIG. 3c shows the bone punches displayed in FIGS. 3a and 3b in a disassembly position.

FIG. 3c shows the bone punches displayed in FIGS. 3a and 3b in a disassembly position 202. In the area of the locking area 230, the bone punches 100 is shown in partial section. The two cylinders 268 are each located distally from the respective bulges 246 associated with them. The first shaft part 220 is located vertically away from the second shaft part 250, which is achieved by the first and second spring arms 241, 242 each being configured to taper distally along the vertical direction 404 and the respective portion of the first shaft part 220 located correspondingly above the first and second spring arms 241, 242 being configured to thicken to the same extent.

Figure 4A:
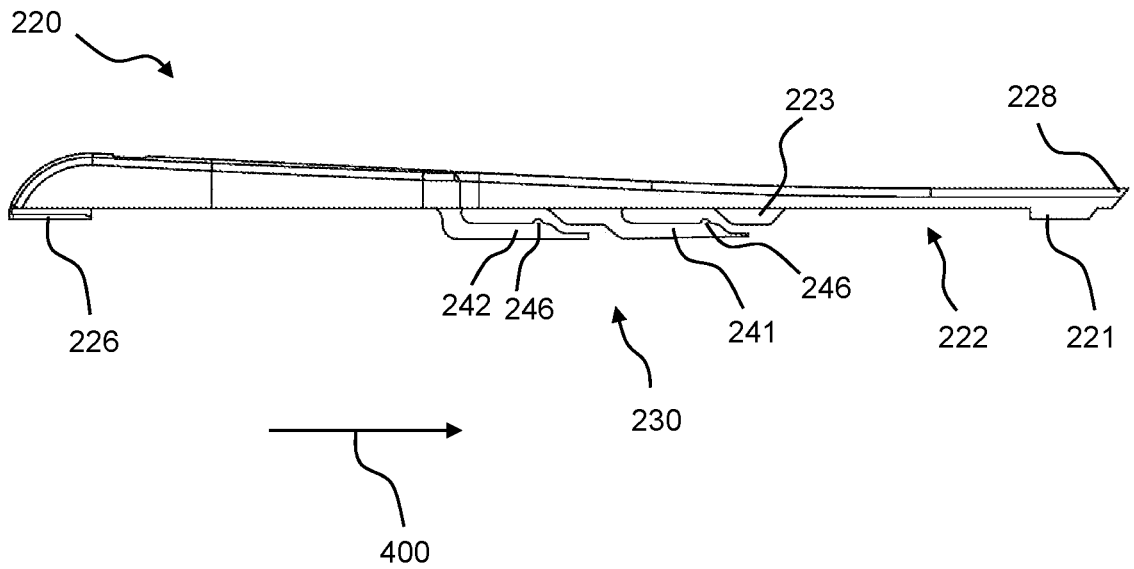
FIG. 4a shows a side view of a first shaft part of the bone punches displayed in FIGS. 3a to 3c.

FIG. 4a shows a first shaft part 220 of the bone punches 100 displayed in FIGS. 3a to 3c in a side view. The first shaft part 220 shown in FIG. 4a is configured similarly to the first shaft part 220 displayed in FIGS. 2a and 2b, with the first shaft part 220 displayed in FIG. 4a comprising only the first guiding elements 221, 222, 223, 226. Instead of the first guiding elements 224, 225 in the first shaft part 220 displayed in FIGS. 2a and 2b, the first and second spring arms 241, 242 and the locking area 230 are provided in the first shaft part 220 displayed in FIG. 4a.

Figure 4B:
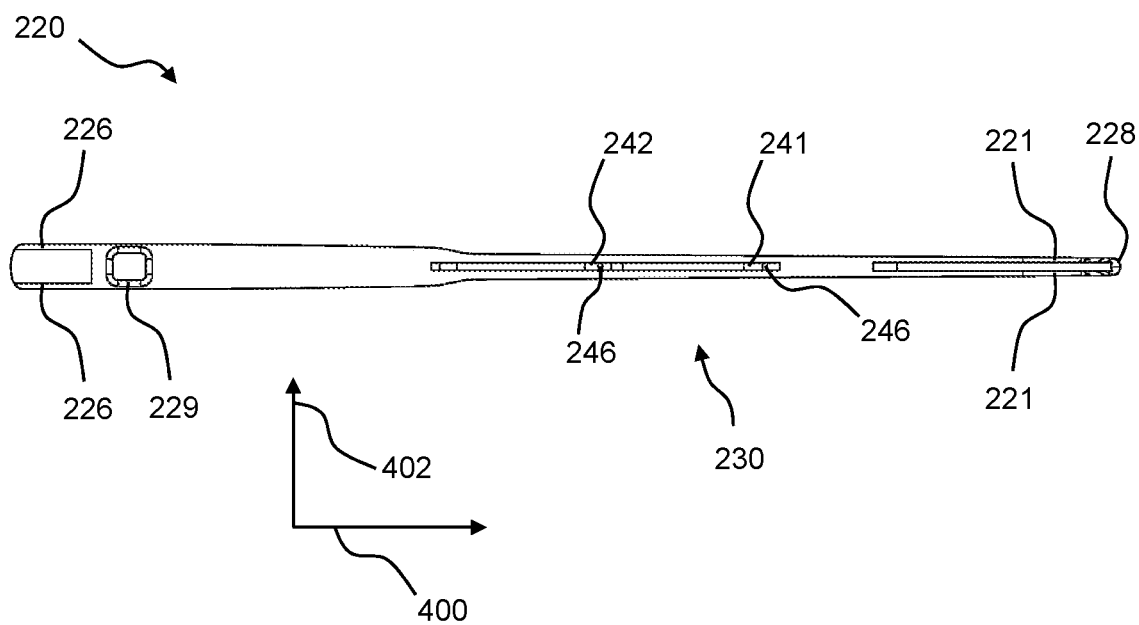
FIG. 4b shows the first shaft part displayed in FIG. 4a from below.

FIG. 4b shows the first shaft part 220 displayed in FIG. 4a from below. The first and second spring arms 241, 242 are centred in the first shaft part 220 with respect to the horizontal direction 402. The first and second spring arms 241, 242 are furthermore configured in such a way that they—like the first guiding elements 224, 225 of the first shaft part 220 displayed in FIGS. 2a and 2b-promote guidance of the first shaft part 220 along the proximal-distal direction 400.

Figure 4C:
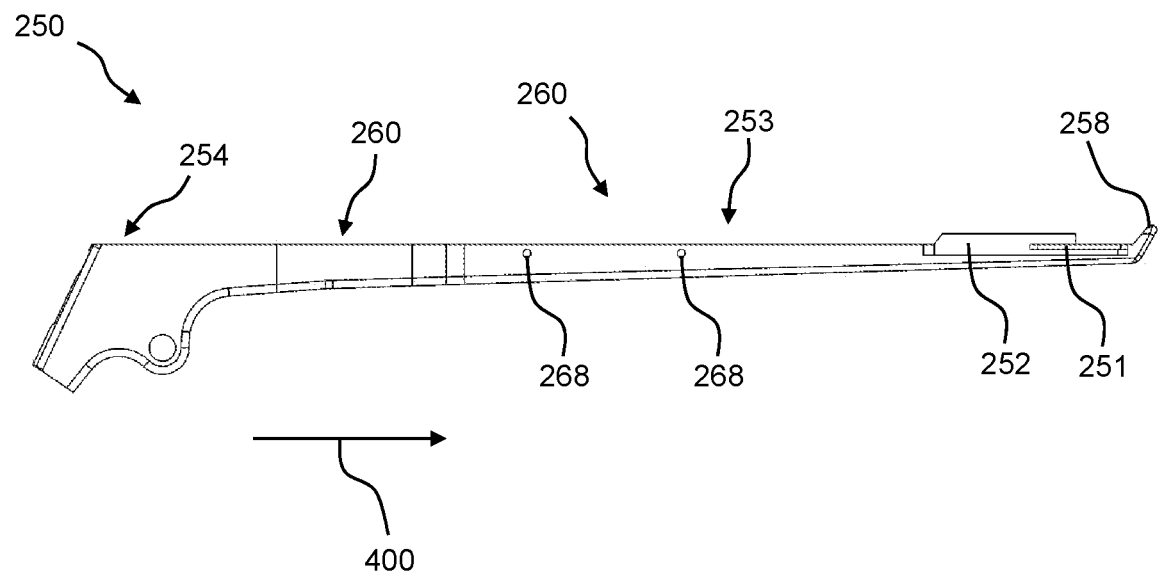
FIG. 4c shows a side view of a second shaft part of the bone punches displayed in FIGS. 3a to 3c.

FIG. 4c shows a second shaft part 250 of the bone punches 100 displayed in FIGS. 3a to 3c in a side view. Compared to the second shaft part 250 displayed in FIGS. 2c and 2d, the second shaft part 250 displayed in FIG. 4c additionally comprises the two cylinders 268 arranged in the second guiding element 253.

Figure 4D:
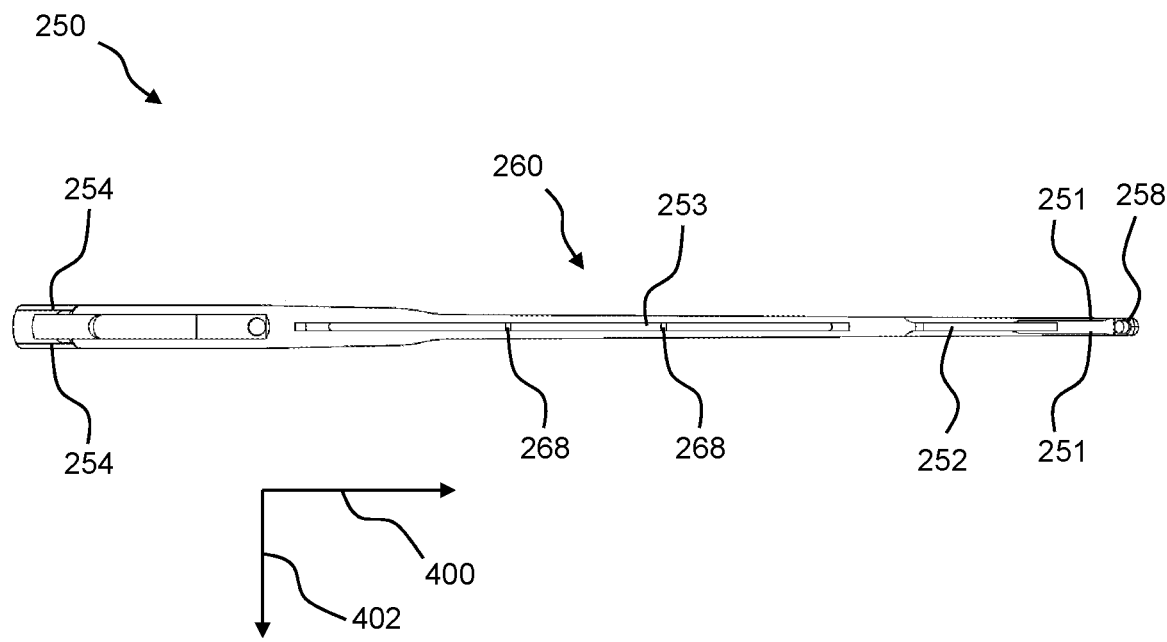
FIG. 4d shows a top view of the second shaft part displayed in FIG. 4c.

FIG. 4d shows the second shaft part 250 displayed in FIG. 4c in a top view. The two cylinders 268 are aligned such that their longitudinal axes run along the horizontal direction 402, i.e. vertical to the proximal-distal direction 400.

Figure 5A:
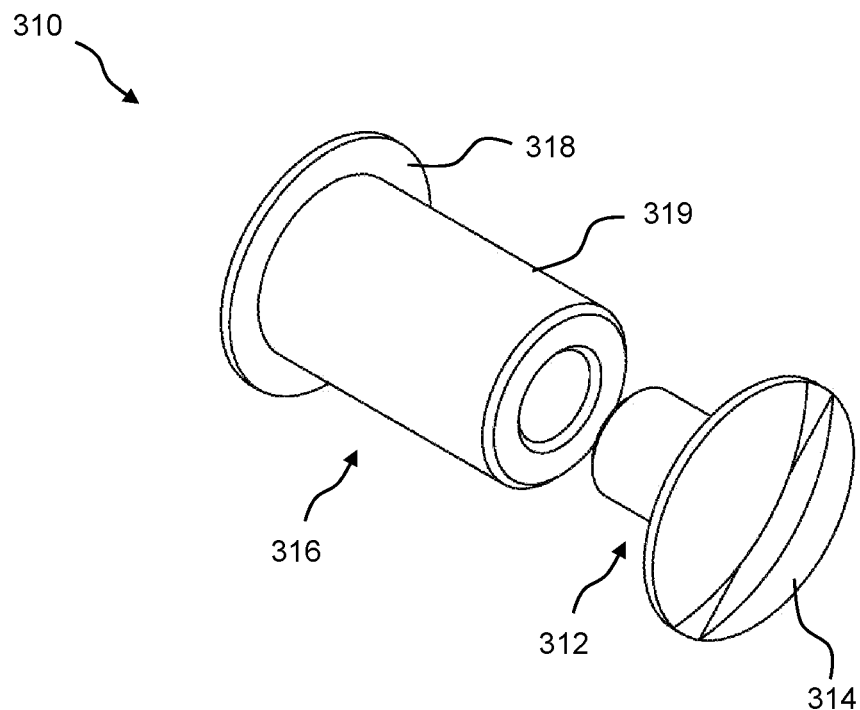
FIG. 5a shows an exploded view of a connecting device of the bone punches displayed in FIGS. 1a to 1e and 3a to 3b, respectively.

FIG. 5a shows an exploded view of a connecting device 310 of the bone punches 100 displayed in FIGS. 1a to 1e and 3a to 3b, respectively. The connecting device 310 comprises a connecting insert 312 and a counter part 316. The connecting insert 312 comprises a stop 314. The counter part 316 comprises a stop 318, too. The counter part 316 further comprises an inlet 319 into which the connecting insert 312 is insertable. The connecting insert 312 can be inserted until its stop 314 abuts the end of the intake 319 opposite the stop 318 of the counter part 316. The connecting device 310 can in particular be provided with a screw device, i.e. the connecting insert 312 further comprises an external thread and the intake 319 a matching internal thread. In this way, a variable and easy-to-use connecting device can be provided. However, a press connection can also be provided for the connecting device 310, i.e. the intake 319 comprises a smaller inner diameter than the connecting insert 312. Furthermore, a welded or riveted connection can also be provided for the connecting device 310.

Figure 5B:
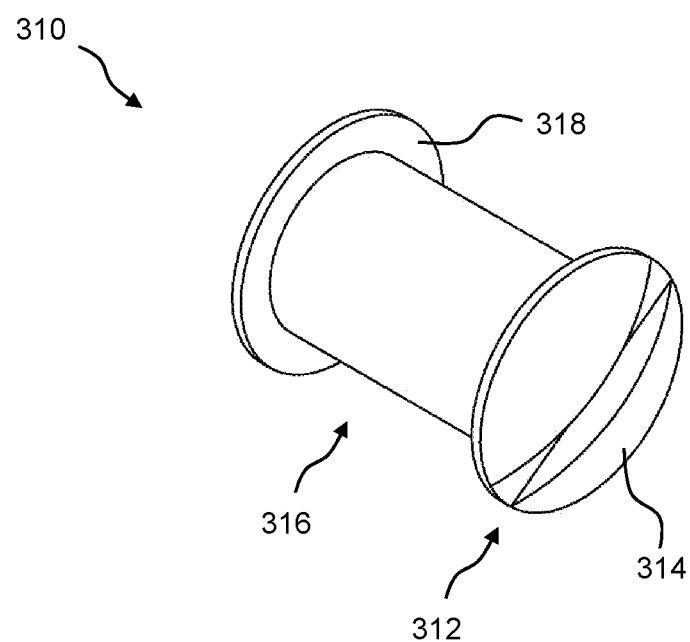
FIG. 5b shows the connecting device displayed in FIG. 5a in the assembled state.

FIG. 5b shows the connecting device 310 displayed in FIG. 5a in the assembled state. The connecting device 310 is configured so that the stops 314, 318 are in clearance-free or nearly clearance-free contact with the outside of the second shaft part 250 in the assembled state. The Intake 319 is configured to support the second shaft part 250 and the first handle portion 320. For this purpose, the outer contour of the intake 319 is configured complementary to the inner contour of the intake 276 of the second shaft part 250 (cf. FIG. 2c) and to the inner contour of the intake 341 of the first handle portion 320 (cf. FIG. 2f) in such a way that, on the one hand, the first handle portion 320 is securely mounted in the second shaft part 250 and, on the other hand, the first handle portion 320 can be rotated with low resistance and low clearance or without clearance in the second shaft part 250.

Figure 5C:
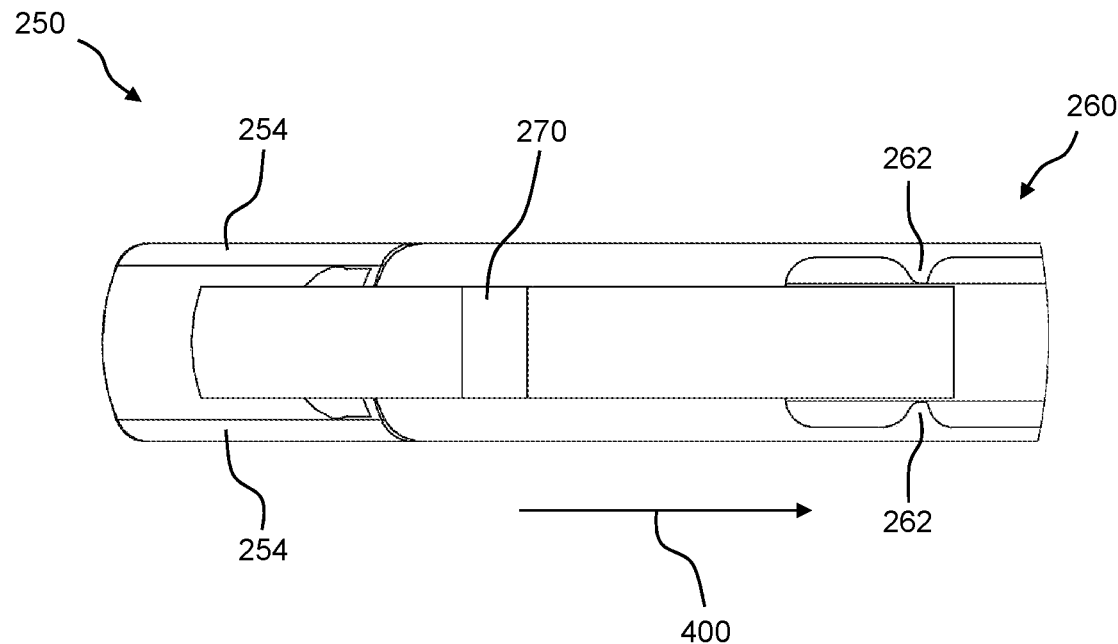
FIG. 5c shows a section of a second shaft part with a first stop element in a top view.

FIG. 5c shows a section of the second shaft part 250 with a first stop element 270 in a top view. Although the figure shows a detail of the second shaft part 250 displayed in FIGS. 2c and 2d, it can also be applied to the second shaft part 250 displayed in FIGS. 4c and 4d. The first stop element 270 is configured for this purpose and arranged in such a way that the movability of the first handle portion 320, in particular the handle head 340, is restricted proximally in the course of the second movement 324. This prevents damage or jamming of the components that move against each other, in particular the first handle portion 320 and the first shaft part 220.

Figure 5D:
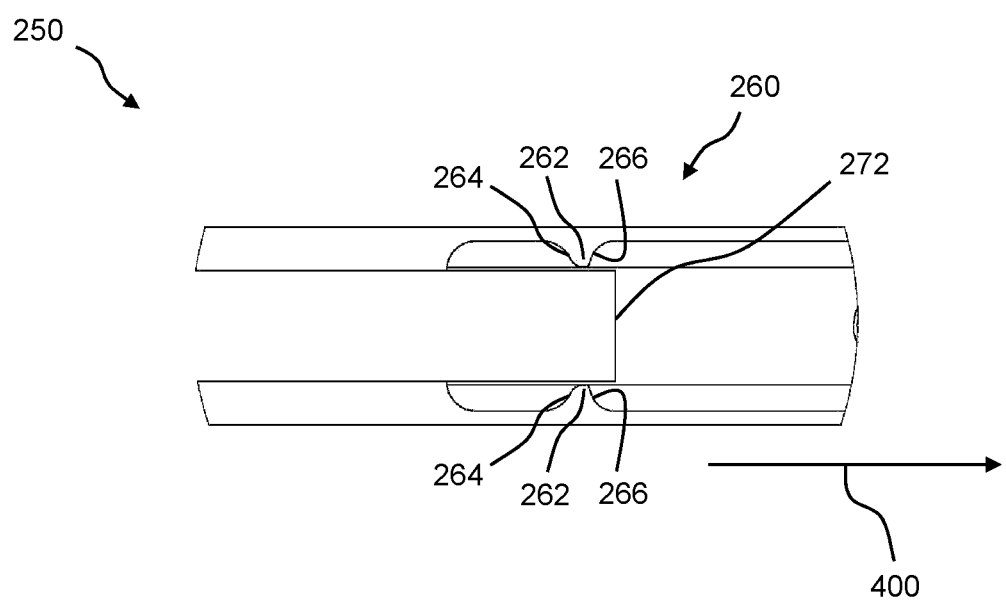
FIG. 5d shows a section of a second shaft part with a second stop element in a top view.

FIG. 5d shows a section of the second shaft part 250 with a second stop element 272 in a top view. Although the figure shows a detail of the second shaft part 250 displayed in FIGS. 2c and 2d, it is equally transferable to the second shaft part 250 displayed in FIGS. 4c and 4d. The second stop element 272 is configured for this purpose and arranged in such a way that the movability of the first handle portion 320, in particular of the handle head 340, is restricted distally in the course of the first movement 322. This prevents damage or jamming of the components that move against each other, in particular the first handle portion 320 and the first shaft part 220. FIG. 5d also shows details of the fixing area 260 and the bulges 262. The two bulges 262 each comprise a proximal edge 264 and a distal edge 266. The two distal edges 266 are formed in such a way that in the neutral position 204 (cf. FIG. 1b), when the projections 244 are guided from distal to proximal in the fixing area 260 in the course of the second movement 324, the projections 244 rest against the distal edges 266 and a further movement of the first shaft part 220 towards the proximal is prevented for the moment. If sufficient force is then applied and the second movement 324 continues, the projections 244 travel along the distal edges 266, causing the first and second spring arms 241, 242 to deflect along and against the horizontal direction 402, respectively. In this way, the unlocking status 234 can be achieved, i.e. the projections 244 can overcome the distal edges 266 and slide along the proximal edges 264 in a proximal direction, causing the shaft 200 to be moved into the disassembly position 202 (cf. FIG. 1c). If the shaft 200 is then to be moved back to the neutral position 204 against the second movement 324, sufficient force must be applied so that the projections 244 can overcome the proximal edges 264. The two proximal edges 264 comprise a smaller slope along the proximal distal direction 400 than the two distal edges 266. This makes it possible to provide greater resistance to moving the shaft 200 from the neutral position 204 to the disassembly position 202 than to moving the shaft 200 from the disassembly position 202 to the neutral position 204. Such proximal and distal edges 264, 266 can also be provided in the first shaft part 220 displayed in FIGS. 4a and 4b (cf. FIG. 6b).

Figure 5E:
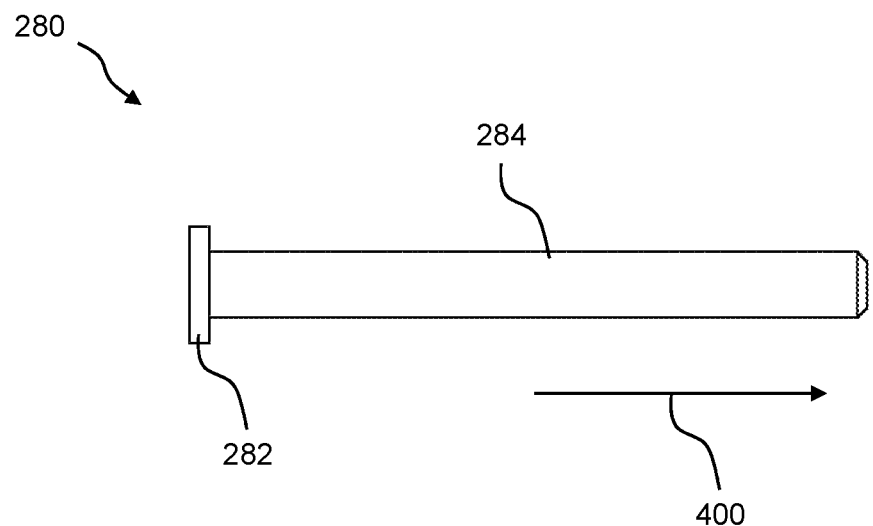
FIG. 5e shows a return member in a side view.

FIG. 5e shows a return member 280 in a side view. The stop 282 is further configured to limit distal penetration of the return member 280 into the guiding opening 274 (cf. FIG. 1e).

Figure 5F:
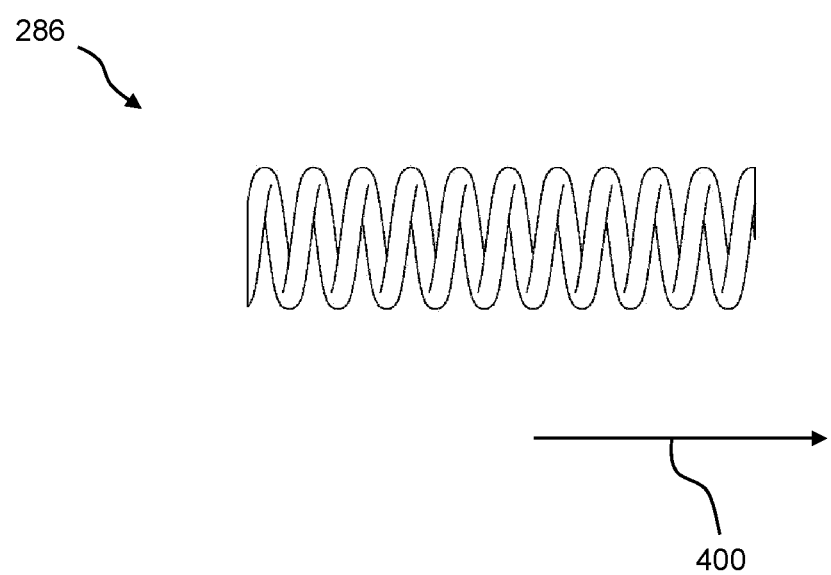
FIG. 5f shows a side view of a spring associated with the return member displayed in FIG. 5e.

FIG. 5f shows a side view of the spring 286 associated with the return member 280 displayed in FIG. 5e. The spring 286 is placed on the shaft 284 (cf. FIG. 1e) and is configured to provide resistance, in particular increasing resistance, to the first movement 322. Furthermore, with the spring 286 it can be achieved that during the main use of the bone punches 100 no force is applied by the operator to reset or move back the shaft 200 from the punching position 206 to the neutral position 204, which can increase the handling.

Figure 6A:
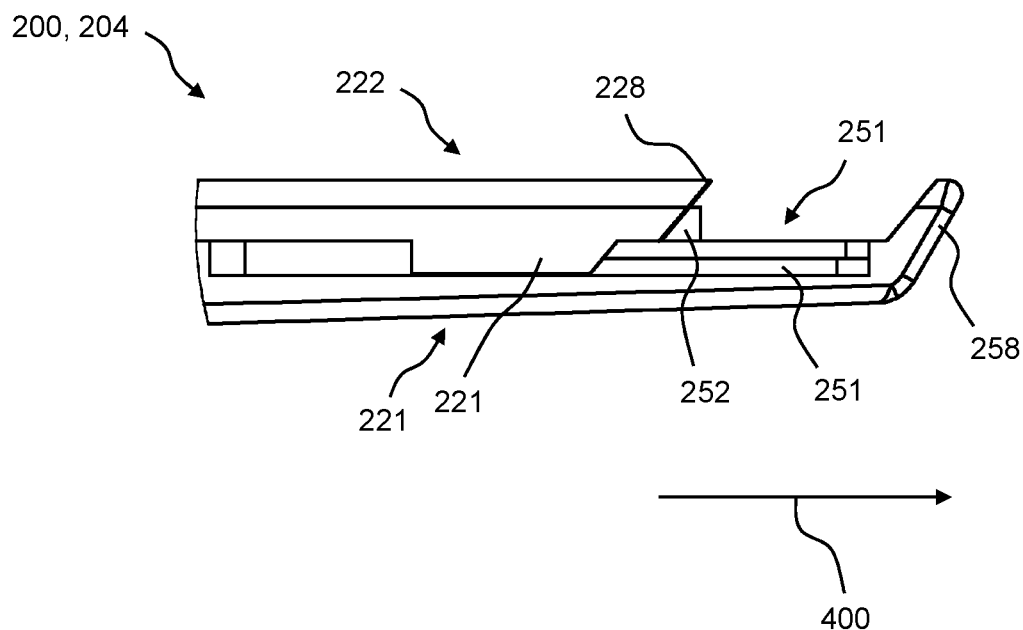
FIG. 6a shows the shaft of the bone punches displayed in FIGS. 1a to 1e and 3a to 3c, respectively, in the neutral position displayed in FIGS. 1b and 3b, respectively, in a distal detailed view.

FIG. 6a shows the shaft 200 of the bone punches 100 displayed in FIGS. 1a to 1e and 3a to 3c, respectively, in the neutral position 204 displayed in FIGS. 1b and 3b, respectively, in a distal detailed view. By means of the cooperation of the two first guiding elements 221 arranged at the distal end with the two second guiding elements 251 arranged at the distal end, secure guiding of the first shaft part 220 in the outer region is made possible, and by means of the cooperation of the first guiding element 222 arranged a bit further proximally and second guiding element 252, secure guiding in the central region is enabled (cf. FIGS. 2a to 2d). Thus, the punching element 228 and the punch intake 258 can be moved towards each other precisely and safely, especially under load.

Figure 6B:
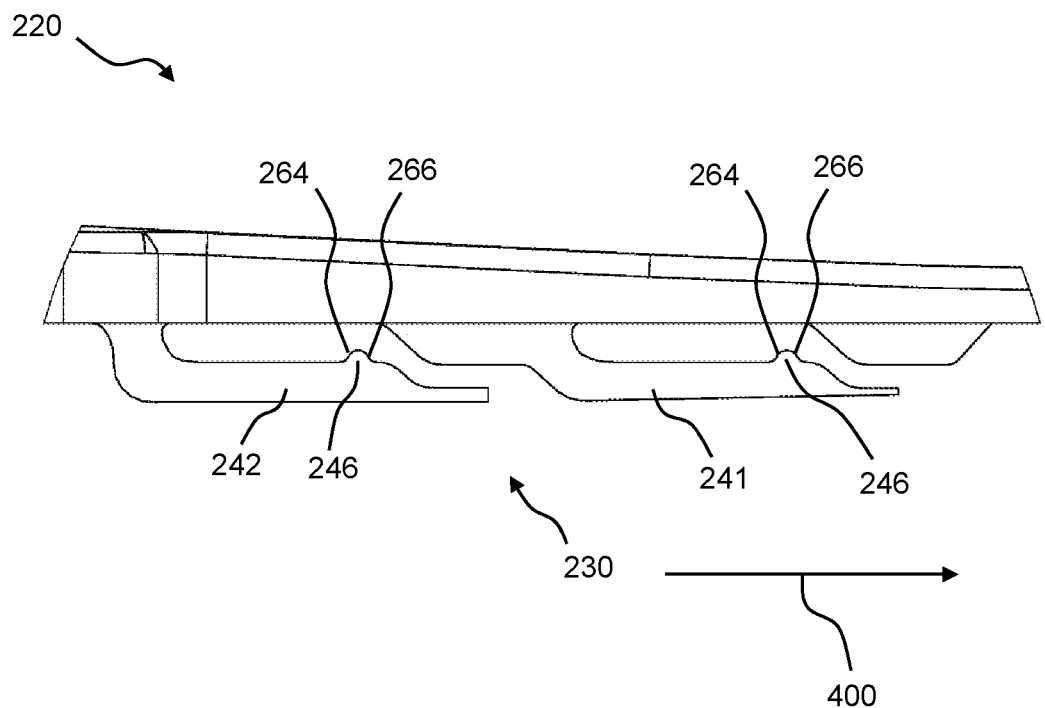
FIG. 6b shows a detailed view of the first shaft part displayed in FIGS. 4a and 4b.

FIG. 6b shows a detailed view of the first shaft part 220 displayed in FIGS. 4a and 4b. The two bulges 246 each comprise a proximal edge 264 and a distal edge 266, wherein in the first shaft part 220 displayed in FIG. 6b, the two proximal edges 264 are overcome with the cylinders 268 to move the shaft 200 into the disassembly position 202, but not the two distal edges 266, as in the second shaft part 250 displayed in FIGS. 5d and 2c and 2d.

Figure 6C:
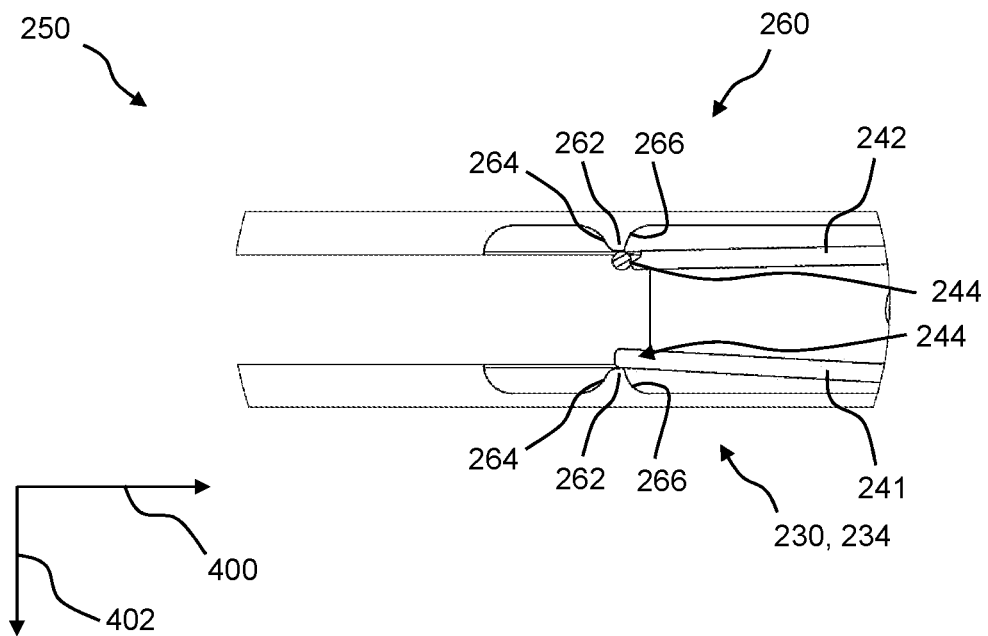
FIG. 6c shows the section of the second shaft part displayed in FIG. 5d with the locking area displayed in FIGS. 1a to 1c and 2a in an unlocking status in a top view.

FIG. 6c shows the section of the second shaft part 250 displayed in FIG. 5d with the locking area 230 displayed in FIGS. 1a to 1c and 2a in the unlocking status 234 in a top view. The first spring arm 241 and the second spring arm 242 are oriented in such a way that the two projections 244 are each located on the tip of the two bulges 262, i.e., between the proximal edge 264 and the distal edge 266. As a result, the first spring arm 241 is oriented opposite to the horizontal direction 402, i.e., inward, and the second spring arm 242 is deflected with the horizontal direction 402, i.e., also inward, allowing the first shaft part 220 to be deflected or displaced further proximally, i.e., against the proximal-distal direction 400. This allows the shaft 200 to be moved from the neutral position 204 to the disassembly position 202 (cf. FIG. 1c).

Figure 6D:
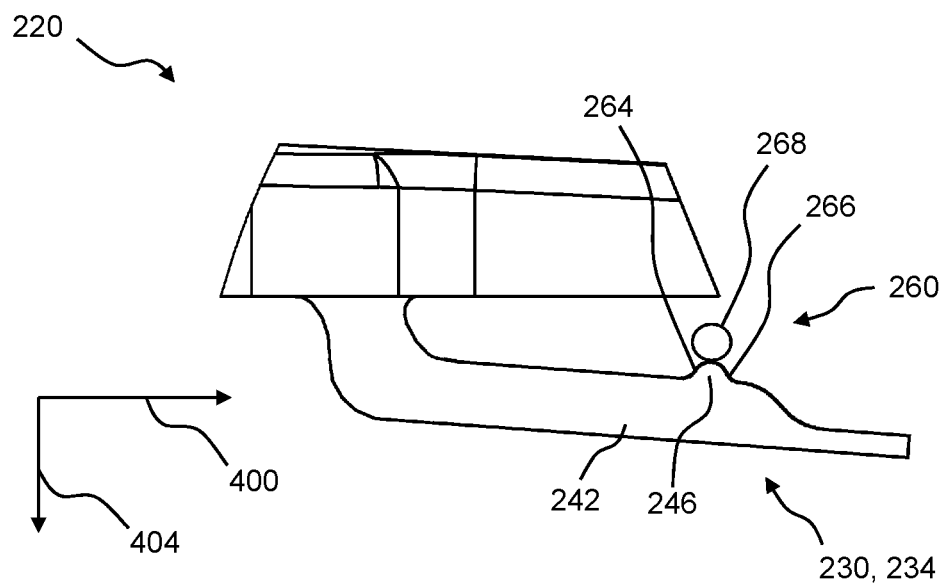
FIG. 6d shows a section of the first shaft part displayed in FIG. 6b with a locking area in an unlocking status.

FIG. 6d shows a section of the first shaft part 220 displayed in FIG. 6b with the locking area 230 in the unlocking status 234. The second spring arm 242 is shown, wherein the illustration and what is described in this context can be applied in the same way to the first spring arm 241. The cylinder 268 is located on the tip of the bulge 246, i.e., between the proximal edge 264 and the distal edge 266, causing the second spring arm 242 to deflect along the vertical direction 404, thereby moving the shaft 200 from the neutral position 204 to the disassembly position 202 (cf. FIGS. 3b and 3c).

Figure 6E:
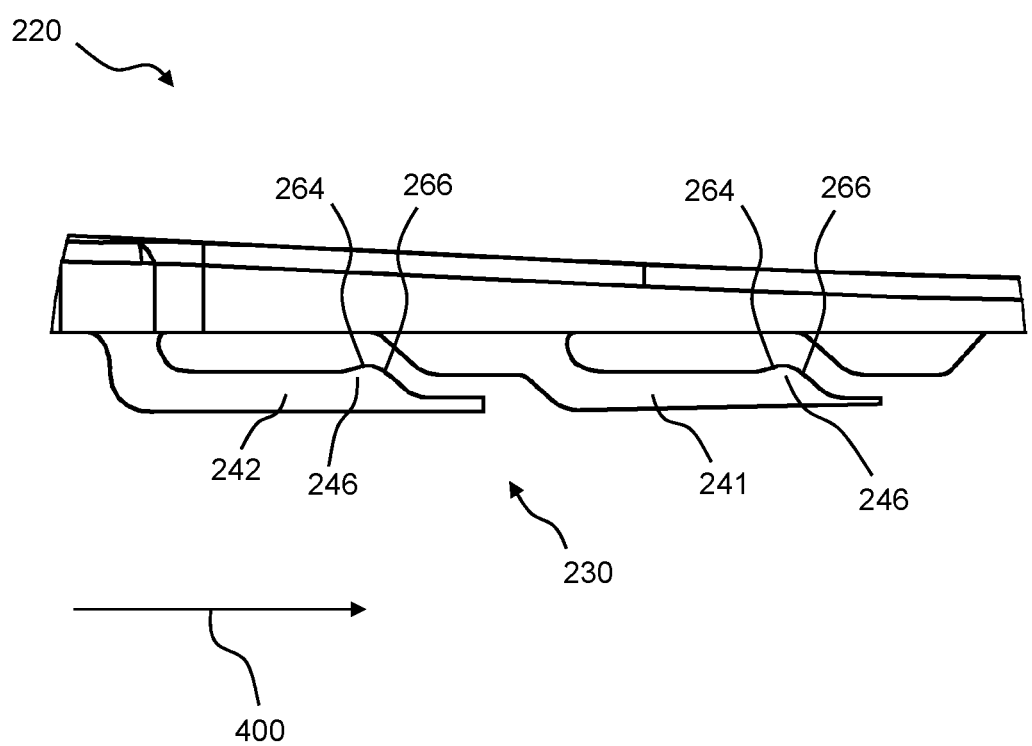
FIG. 6e shows an alternative to the first shaft part displayed in FIG. 6b.

FIG. 6e shows an alternative to the first shaft part 220 displayed in FIG. 6b. The two bulges 246 shown here are more voluminous and each comprise a proximal edge 264 and a distal edge 266 with a smaller pitch than the two bulges 246 or proximal edges 264 and distal edges 266, respectively displayed in FIG. 6b. The lower slope of the proximal edges 264 can provide less resistance to moving the locking area 230 to the unlocking position 234, thereby facilitating handling. With the increased volume of the two bulges 246, it can be achieved that their lifetime is increased.

REFERENCE SIGNS LIST 100 bone punches
200 shaft
202 disassembly position
204 neutral position
206 punching position
220 first shaft part
221 first guiding element
222 first guiding element
223 first guiding element
224 first guiding element
225 first guiding element
226 first guiding element
228 punching element
229 guiding opening
230 locking area
232 neutral status
234 unlocking status
240 spring area
241 first spring arm
242 second spring arm
244 projection
246 bulge
248 undercut
250 second shaft part
251 second guiding element
252 second guiding element
253 second guiding element
254 second guiding element
258 punch intake
260 fixing area
262 bulge
264 proximal edge
266 distal edge
268 cylinder
270 first stop element
272 second stop element 274 guiding opening
276 intake
280 return member
282 stop
284 shaft
286 spring
300 handle
310 connecting device
312 connecting insert
314 stop
316 counter part
318 stop
319 intake
320 first handle portion
322 first movement
324 second movement
326 protrusion
330 first handle side
332 second handle side
340 handle head
341 intake
342 recess
344 first load transfer area
346 second load transfer area
348 third load transfer area
350 second handle portion
352 plug element
356 protrusion
360 first handle side
362 second handle side
400 proximal-distal direction
402 horizontal direction
404 vertical direction
410-410 sectional view

The invention claimed is:

1. A disassemblable bone punch comprising a shaft and a handle, wherein
the shaft comprises a first shaft part and a second shaft part, wherein the first shaft part comprises at least one first guiding element, and the second shaft part comprises at least one second guiding element, wherein the first shaft part is connected to the second shaft part such that the first guiding element is in engagement with the second guiding element and the first shaft part is movable relative to the second shaft part parallel to a proximal-to-distal direction relative to the second shaft part, wherein
the shaft is movable into a disassembly position, into a neutral position and into a punching position, wherein
the handle comprises a first handle portion and a second handle portion, wherein the first handle portion is movably connected to the second shaft part, wherein the second handle portion is connected to the second shaft part, wherein by a first movement of the first handle portion the shaft is displaceable from the neutral position into the punching position,
wherein by a second movement of the first handle portion the shaft is displaceable from the neutral position into the disassembly position, wherein
the first shaft part comprises a locking area, and
wherein the locking area is movable from a neutral status to an unlocking status, wherein the locking area is configured such that, when the locking area is in the neutral status, moving of the shaft into the disassembly position is prevented and, by the second movement, the locking area is simultaneously moved into the unlocking status and the shaft is moved into the disassembly position; and
wherein the locking area comprises a deflectable spring area, and wherein the locking area is movable into the unlocking status by deflecting the spring area.

2. The disassemblable bone punch according to claim 1, wherein the spring area is configured to be deflectable substantially perpendicular to the proximal-to-distal direction.

3. The disassemblable bone punch according to claim 2, wherein the spring area is deflectable substantially parallel to a horizontal direction.

4. The disassemblable bone punch according to claim 2, wherein the spring area is deflectable substantially parallel to a vertical direction.

5. The disassemblable bone punch according to claim 1, wherein the spring area comprises a recess.

6. The disassemblable bone punch according to claim 1, wherein the second shaft part comprises a fixing area, the fixing area being configured and arranged to interact with the locking area such that if the locking area is in the neutral status, additional resistance is provided by the fixing area opposing the second movement of the shaft into the disassembly position.

7. The disassemblable bone punch according to claim 6, wherein the locking area comprises at least one first resistance element and/or the fixing area comprises at least one second resistance element, wherein the first resistance element and/or the second resistance element is/are arranged and configured such that an additional resistance opposes the movement of the locking area into the unlocking status.

8. The disassemblable bone punch according to claim 7, comprising a first resistance element and a second resistance element, wherein the first resistance element and the second resistance element are interactively arranged and configured such that additional resistance opposes the movement of the locking area into the unlocking status.

9. The disassemblable bone punch according to claim 8, wherein the first resistance element is configured as a projection and/or the second resistance element is configured as a bulge.

10. The disassemblable bone punch according to claim 8, wherein the first resistance element is configured as a bulge and/or the second resistance element is configured as a cylinder.

11. The disassemblable bone punch according to claim 1, wherein the bone punch further comprises a first stop element preferably arranged in the second shaft part, wherein the first stop element is configured and further arranged such that a movability of the first handle portion is limited proximally.

12. The disassemblable bone punch according to claim 1, wherein the bone punch further comprises a second stop element arranged in the second shaft portion, wherein the second stop element is configured and further arranged such that a movability of the first handle portion is limited distally.

13. The disassemblable bone punch according to claim 1, wherein the bone punch further comprises a return member preferably arranged in the second shaft part, wherein the return member is configured and further arranged such that after performing the first movement, the shaft is automatically displaced from the punching position back to the neutral position and, the first movement is opposed by an increasing resistance.

* * * * *